United States Patent [19]
Klein et al.

[11] Patent Number: 5,866,685
[45] Date of Patent: Feb. 2, 1999

[54] ANTITHROMBOTIC AZACYCLOALKYLALKANOYL PEPTIDES AND PSEUDOPEPTIDES

[75] Inventors: Scott I. Klein, Norristown; Bruce F. Molino, Hatfield, both of Pa.

[73] Assignee: Rhone-Poulenc Rorer Pharmaceuticals Inc., Collegeville, Pa.

[21] Appl. No.: 628,648

[22] PCT Filed: Oct. 17, 1994

[86] PCT No.: PCT/US94/12135

§ 371 Date: May 2, 1996

§ 102(e) Date: May 2, 1996

[87] PCT Pub. No.: WO95/10295

PCT Pub. Date: Apr. 20, 1995

Related U.S. Application Data

[63] Continuation-in-part of Ser. No. 138,820, Oct. 15, 1993, abandoned.

[51] Int. Cl.⁶ .................................................. A61K 38/06
[52] U.S. Cl. .............................. 530/331; 514/18; 514/19; 530/330
[58] Field of Search ........................ 514/18, 19; 530/331, 530/330

[56] References Cited

U.S. PATENT DOCUMENTS

| | | | |
|---|---|---|---|
| 4,683,291 | 7/1987 | Zimmerman et al. | 530/324 |
| 4,857,508 | 8/1989 | Adams et al. | 514/18 |
| 4,879,313 | 11/1989 | Tjoeng et al. | 514/616 |
| 4,992,463 | 2/1991 | Tjoeng et al. | 514/438 |
| 5,023,233 | 6/1991 | Nutt et al. | 514/11 |
| 5,037,808 | 8/1991 | Tjoeng et al. | 514/20 |

FOREIGN PATENT DOCUMENTS

| | | |
|---|---|---|
| 0 319 506 B1 | 6/1989 | European Pat. Off. . |
| 2 608 160 | 6/1988 | France . |
| WO 91/04746 | 4/1991 | WIPO . |
| WO 92/18117 | 10/1992 | WIPO . |
| WO 95/10295 | 4/1995 | WIPO . |

OTHER PUBLICATIONS

Plow et al., Inhibition of fibrinogen binding to human platelets by the tetrapeptide glycyl–L–prolyl–L–arginyl–L–proline, Proc.Natl.Acad.Sci., vol. 79, pp. 3711–3715 (Jun. 1982).

Ginsberg et al., Inhibition of Fibronectin Binding to Platelets by Proteolytic Fragments and Synthetic Peptides Which Support Fibroblast, J.Bio.Chem., vol. 260, No. 7, pp. 3931–3936 (Apr. 10, 1985).

Haverstick et al., Inhibition of Platelet Adhesion to Fibronectin, Fibrinogen, and von Willebrand Factor Substrates by a Synthetic Tetrapeptide Derived from the Cell–Binding Domain of Fibronectin, Blood, vol. 66, No. 4, pp. 946–952 (Oct. 1985).

Gartner et al., The Tetrapeptide Analogue of the Cell Attachment Site of Fibronectin Inhibits Platelet Aggregation and Fibrinogen Binding to Activated Platelets, J.Bio.Chem., vol. 260, No. 22, pp. 11891–11894 (Oct. 5, 1985).

Plow et al., The effect of Arg–Gly–Asp–Containing peptides on fibrinogen and on Willebrand factor binding to platelets, Natl.Acad.Sci., vol. 82, pp. 8057–8061 (Dec. 1985).

Ruoslahti et al., Arg–Gly–Asp: A Versatile Cell Recognition Signal, Cell, vol. 44, pp. 517–518 (Feb. 28, 1986).

Ruggeri et al., Inhibition of platelet function with synthetic peptides designed to be high–affinity antagonists of fibrinogen binding to platelets, Proc.Natl.Acad.Sci., vol. 83, pp. 5708–5712 (Aug. 1986).

*Primary Examiner*—Cecilia J. Tsang
*Assistant Examiner*—David Lukton
*Attorney, Agent, or Firm*—Michael B. Martin; Raymond S. Parker, III; Paul R. Darkes

[57] ABSTRACT

The present invention relates to azacycloalkylalkanoyl peptides and pseudopeptides which inhibit platelet aggregation and thrombus formation thereby being useful in the prevention and treatment of thrombosis associated with disease states such as myocardial infarction, stroke, peripheral arterial disease, and disseminated intravascular coagulation, to methods for the prevention or treatment of thrombosis in a mammal in need of such therapy comprising the administration of a therapeutically effective amount of such compounds, and to pharmaceutical compositions comprising such compounds.

35 Claims, No Drawings

ANTITHROMBOTIC AZACYCLOALKYLALKANOYL PEPTIDES AND PSEUDOPEPTIDES

This application is a 371 of PCT/US94/12135, filed Oct. 17, 1994, which is a continuation-in-part application of co-pending U.S. application Ser. No. 08/138,820, filed Oct. 15, 1993 abandoned.

BACKGROUND OF INVENTION

1. Field of Invention

This invention relates to compounds having antithrombotic activity. More particularly, the invention relates to azacycloalkylalkanoyl peptides and pseudopeptides that inhibit platelet aggregation and thrombus formation in mammals and which are useful in the prevention and treatment of thrombosis associated with disease states such as myocardial infarction, stroke, peripheral arterial disease and disseminated intravascular coagulation.

Haemostasis, the biochemistry of blood coagulation, is an extremely complex phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of adhesive glycoproteins, i.e., fibrinogen, fibronectin, and von Willebrand factor. Fibrinogen is a co-factor for platelet aggregation, while fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane protein complex known as glycoprotein IIb/IIIa.

Adhesive glycoproteins, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. Compounds within the scope of the present invention block the fibrinogen receptor, thus inhibiting platelet aggregation and subsequent thrombus formation and when administered in the form of pharmaceutical compositions comprising such compounds are useful for the prevention and treatment of thrombogenic diseases, such as myocardial infarction, stroke, peripheral arterial disease and disseminated intravascular coagulation.

2. Reported Developments

It has been observed that the presence of Arg-Gly-Asp (RGD) is necessary in fibrinogen, fibronectin and von Willebrand factor for their interaction with the cell surface receptor (Ruoslahti E., Pierschbacher, *Cell* 1986, 44, 517–18). Two other amino acid sequences also seem to take part in the platelet attachment function of fibrinogen, namely, the Gly-Pro-Arg sequence, and the dodecapeptide, His-His-Leu-Gly-Gly-Ala-Lys-Gln-Ala-Gly-Asp-Val sequence. Small synthetic peptides containing the RGD or dodecapeptide have been shown to bind to the platelet GPIIb/IIIa receptor and competitively inhibit binding of fibrinogen, fibronectin and von Willebrand factor as well as inhibit aggregation of activated platelets (Plow, et al., *Proc. Natl. Acad. Sci. USA* 1985, 82, 8057–61; Ruggeri, et al., *Proc. Natl. Acad. Sci. USA* 1986, 5708–12; Ginsberg, et al., *J. Biol. Chem.* 1985, 260, 3931–36; and Gartner, et al., *J. Biol. Chem.* 1987, 260,11,891–94).

Indolyl compounds containing guanidinoalkanoyl- and guandinoalkenoyl- aspartyl moieties are reported to be platelet-aggregation inhibitors by Tjoeng, et al., U.S. Pat. Nos. 5,037,808 and 4,879,313.

U.S. Pat. No. 4,992,463 (Tjoeng, et al.), issued Feb. 12, 1991, discloses generically that a series of aryl and aralkyl guanidinoalkyl peptide mimetic compounds exhibit platelet aggregation inhibiting activity and discloses specifically a series of mono- and dimethoxy phenyl peptide mimetic compounds and a biphenylalkyl peptide mimetic compound.

U.S. Pat. No. 4,857,508 (Adams, et al.), issued Aug. 15,1989, discloses generically that a series of guandinoalkyl peptide derivatives containing terminal aralkyl substituents exhibit platelet aggregation inhibiting activity and discloses specifically a series of O-methyl tyrosine, biphenyl, and naphthyl derivatives containing a terminal amide functionality.

Haverstick, D. M., et al., in *Blood* 66 (4), 946–952 (1985), disclose that a number of synthetic peptides, including arg-gly-asp-ser and gly-arg-gly-asp-ser, are capable of inhibiting thrombin-induced platelet aggregation.

Plow, E. F., et al., in *Proc. Natl. Acad. Sci. USA* 79, 3711–3715 (1982), disclose that the tetrapeptide glycyl-L-prolyl-L-arginyl-L-proline inhibits fibrinogen binding to human platelets.

French Application No. 86/17507, filed Dec. 15, 1986, discloses that tetra-, penta- and hexapeptide derivatives containing the -arg-gly-asp-sequence are useful as antithrombotics.

U.S. Pat. No. 4,683,291 (Zimmerman, et al.), issued Jul. 28, 1987, discloses that a series of peptides, comprised of from six to forty amino acids, which contain the sequence -arg-gly-asp- are platelet binding inhibitors.

European Application Publication No. 0 319 506, published Jun. 7, 1989, discloses that a series of tetra-, penta-, and hexapeptide derivatives containing the -arg-gly-asp-sequence are platelet aggregation inhibitors.

Cyclic peptide analogues containing the moiety Gly-Asp are reported to be fibrinogen receptor antagonists in U.S. Pat. No. 5,023,233.

Peptides and pseudopeptides containing amino-, guanidino-, imidizaloyl, and/or amidinoalkanoyl, and alkenoyl moieties are reported to be antithrombotic agents in pending U.S. applications Ser. Nos. 07/677,006, 07/534,385, and 07/460,777 filed on Mar. 28, 1991, Jun. 7, 1990, and Jan. 4, 1990, respectively, as well as in U.S. Pat. No. 4,952,562, and in International Application No. PCT/US90/05448, filed Sep. 25, 1990, all assigned to the same assignee as the present invention.

Peptides and pseudopeptides containing amino- and guanidino- alkyl- and alkenyl- benzoyl, phenylalkanoyl, and phenylalkenoyl moieties are reported to be antithrombotic agents in pending U.S. application Ser. No. 07/475,043, filed Feb. 5, 1990, and in International Application No. PCT/US91/02471, filed Apr. 11, 1991, published as International Publication No. WO 92/13117 Oct. 29, 1992, assigned to the same assignee as the present invention.

Alkanoyl and substituted alkanoyl azacycloalkylformyl aspartic acid derivatives are reported to be platelet aggregation inhibitors in U.S. Pat. No. 5,053,392, filed Dec. 1, 1989, and assigned to the same assignee and having the same inventorship as the present invention.

N-subsituted azacycloalkylcarbonyl cyclic aminoacylaspartic acid derivatives are reported to be antithrombotics in U.S. Pat. No. 5,064,814, filed Apr. 5, 1990 by the same inventors and assigned to the same assignee as the present invention. Azacycloalkylformylglycyl aspartic acid derivatives are reported to be antithrombotics in U.S. Pat. No. 5,051,405, filed Oct. 10, 1989, and assigned to the same assignee as the present invention.

European Patent Application 0479,481, published Apr. 8, 1992, discloses azacycloalkyalkanoyl glycyl aspartyl amino acids as fibrinogen receptor antagonists.

European Patent Application 0478,362, published Apr. 1, 1992, discloses azacycloalkyalkanoyl peptidyl β-alanines as fibrinogen receptor antagonists.

The present invention relates to azacycloalkylalkanoyl peptides and pseudopeptides which inhibit platelet aggregation and thrombus formation.

SUMMARY OF THE INVENTION

Compounds of the present invention are described by Formula I

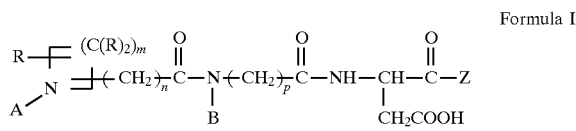

wherein:

A is -H, amidino, or substituted amidino;

B is alkyl, cycloalkyl, cycloalkylalkyl, alkylcycloalkyl, alkyycycloalkylalkyl, aryl, aralkyl, alkylaryl, or alkylaralkyl;

Z is 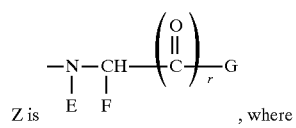, where

E is -H or, in combination with F, forms a 4-, 5-, 6-, or 7-membered azacycloalkane ring, F is the α-carbon side chain of a naturally occuring α-amino acid, -H, alkyl, cycloalkyl, cycloalkylalkyl, alkylcycloalkyl, alkylcycloalkylalkyl, aryl, substituted aryl, aralkyl, substitued aralkyl, heterocyclyl, substituted heterocyclyl, heterocyclylalkyl, substituted heterocyclylalkyl, or, in combination with E, forms a 4-, 5-, 6-, or 7-membered azacycloalkane ring, G is alkyl, cycloalkyl, cycloalkylalkyl, alkylcycloalkyl, alkylcycloalkylalkyl, aryl, substituted aryl, aralkyl, substituted aralkyl, heterocyclyl, substituted heterocyclyl, heterocyclylalkyl, substituted heterocyclylalkyl, $OR^1$, or $NR^1R^2$, where $R^1$ and $R^2$ are independently -H, alkyl, cycloalkyl, cycloalkylalkyl, alkylcycloalkyl, alkylcycloalkylalkyl, aryl, aralkyl, alkylaryl, or alkylaralkyl, and r is 0 or 1;

R is H-, alkyl, aryl, or aralkyl;

m is 1 to 5;

n is 0 to 6; and p is 1 to 4;

or a pharmaceutically acceptable salt thereof.

Additionally, the present invention relates to pharmaceutical compositions comprising such compounds, and to methods of prevention or treatment of thrombosis in a mammal in need of such therapy comprising the administration of such compounds and pharmaceutical compositions.

The present invention is characterized by the marked and prolonged antithrombotic activity of the compounds of Formula I, above, observed after oral administration thereof.

DETAILED DESCRIPTION OF INVENTION

As used above, and throughout the description of this invention, the following terms, unless otherwise indicated, shall be understood to have the following meanings:

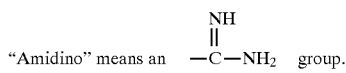

"Substituted amidino" means an amidino group N-substituted on one or both nitrogens by one or more alkyl, cycloalkyl, cycloalkylalkyl, alkycycloalkyl, alkylcycloalkylalkyl, aryl or aralkyl groups.

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain. Preferred straight or branched alkyl groups are the "lower alkyl" groups which are those alkyl groups having from 1 to about 10 carbon atoms. Most preferred lower alkyl groups have from 1 to about 6 carbon atoms.

"Cycloalkyl" means a saturated carbocyclic group having one or more rings and having about 3 to about 10 carbon atoms. Preferred cycloalkyl groups include cyclopropyl, cyclobutyl, cyclopentyl, cyclohexyl, cycloheptyl, and decahydronaphthyl.

"Cycloalkylalkyl means an alkyl group substituted with a cycloalkyl group. Preferred cycloalkylalkyl groups include cyclopentylmethyl, cyclohexylmethyl, cyclohexylethyl, decahydronaphth-1-ylmethyl and decahydronaphth-2-ylmethyl.

"Alkylcycloalkyl" means an cycloalkyl group substituted with an alkyl group. Exemplary alkylcycloalkyl groups include 1-, 2-, 3-, or 4-methyl or ethyl cyclohexyl.

"Alkylcycloalkylalkyl" means an alkyl group substituted by an alkylcycloalkyl group. Exemplary alkylcycloalkyl groups include 1-, 2-, 3-, or 4-methyl or ethyl cyclohexylmethyl or 1-, 2-, 3-, or 4-methyl or ethyl cyclohexylethyl.

"Azacycloalkane" means a saturated aliphatic ring containing a nitrogen atom. Preferred azacycloalkanes include pyrollidine and piperidine.

"Naturally occuring α-amino acid" means glycine, alanine, valine, leucine, isoleucine, serine, threonine, phenylalanine, tyrosine, tryptophan, cysteine, methionine, proline, hydroxyproline, aspartic acid, asparagine, glutamine, glutamic acid, histidine, arginine, ornithine, and lysine.

"α-carbon side chain of a naturally occuring α-amino acid" means the moiety which substitutes the x-carbon of a naturally occuring α-amino acid. Exemplary α-carbon side chains of naturally occuring α-amino acids include isopropyl, methyl, and carboxymethyl for valine, alanine, and aspartic acid, respectively.

"Aryl" means a phenyl or naphthyl group.

"Substituted aryl" means a phenyl or naphthyl group substituted by one or more aryl group substitutents which may be the same or different, where "aryl group substituent" includes alkyl, alkenyl, alkynyl, aryl, aralkyl, hydroxy, alkoxy, aryloxy, aralkoxy, hydroxyalkyl, acyl, formyl, carboxy, alkenoyl, aroyl, halo, nitro, trihalomethyl, cyano, alkoxycarbonyl, aryloxycarbonyl, aralkoxycarbonyl, acylamino, aroylamino, carbamoyl, alkylcarbamoyl, dialkylcarbamoyl, arylcarbamoyl, aralkylcarbamoyl, alkylsulfonyl, alkylsulfinyl, arylsulfonyl, arylsulfinyl, aralkylsulfonyl, aralkylsulfinyl, or -NR$_a$R$_b$ where Ra and R$_b$ are independently hydrogen, alkyl, aryl, or aralkyl.

"Aralkyl" means an alkyl group substituted by an aryl radical. Preferred aralkyl groups include benzyl, naphth-1-ylmethyl naphth-2-ylmethyl, and phenethyl.

"Substituted aralkyl" means an aralkyl group substituted on the aryl portion by one or more aryl group substituents.

"Heterocyclyl" means about a 4- to about a 15-membered monocyclic or multicyclic ring system in which one or more of the atoms in the ring is an element other than carbon, for example nitrogen, oxygen, or sulfur. Preferred heterocyclyl groups include pyridyl, pyrimidyl, and pyrrolidyl.

"Substituted heterocyclyl" means a heterocyclyl group substituted by one or more aryl group substituents.

"Heterocyclylalkyl" and "substituted heterocyclylalkyl" means an alkyl group which is substituted by a heterocyclyl and substituted heterocyclyl group, respectively.

A preferred class of compounds of the present invention is described by Formula I wherein F is -H, alkyl, hydroxymethyl, 1-hydroxyethyl, mercaptomethyl, 2-methylthioethyl, carboxymethyl, 2-carboxyethyl, 4-aminobutyl, 3-guanidinopropyl, cycloalkyl, cycloalkylalkyl, alkylcycloalkyl, alkylcycloalkylalkyl, aryl, substituted aryl, aralkyl, substituted aralkyl, heterocyclyl, substituted heterocyclyl, heterocyclylalkyl, substituted heterocyclylalkyl, or, in combination with E, forms a 4-, 5-, 6-, or 7-membered azacycloalkane ring, provided that heterocyclylalkyl is other than indol-3-ylmethyl.

A more preferred class of compounds of the present invention is described by the preferred class of compounds wherein F is -H, alkyl, hydroxymethyl, 1-hydroxyethyl, mercaptomethyl, 2-methylthioethyl, carboxymethyl, 2-carboxyethyl, 4-aminobutyl, 3-guanidinopropyl, cycloalkyl, cycloalkylalkyl, alkylcycloalkyl, alkylcycloalkylalkyl, aryl, substituted aryl, aralkyl, substituted aralkyl, or, in combination with E, forms a 4-, 5-, 6-, or 7-membered azacycloalkane ring.

A still more preferred class of compounds of the present invention is described by the more preferred class of compounds wherein F is -H, alkyl, hydroxymethyl, 1-hydroxyethyl, mercaptomethyl, 2-methylthioethyl, carboxymethyl, 2-carboxyethyl, 4-aminobutyl, 3-guanidinopropyl, cycloalkyl, cycloalkylalkyl, alkylcycloalkyl, alkylcycloalkylalkyl, or, in combination with E, forms a 4-, 5-, 6-, or 7-membered azacycloalkane ring.

A most preferred class of compounds of the present invention is described by the still more preferred class of compounds wherein B is alkyl, cycloalkyl, cycloalkylalkyl, alkylcycloalkyl, or alkylcycloalkylalkyl A special embodiment of the present invention is described by Formula II $$\underset{A}{\overset{(CH_2)_m}{\underset{|}{N}}}\!\!=\!\!(CH_2)_n\!-\!\overset{O}{\overset{\|}{C}}\!-\!\underset{B}{\overset{|}{N}}\!-\!(CH_2)_p\!-\!\overset{O}{\overset{\|}{C}}\!-\!NH\!-\!\underset{CH_2COOH}{\overset{|}{CH}}\!-\!\overset{O}{\overset{\|}{C}}\!-\!NH\!-\!\underset{J}{\overset{|}{CH}}\!-\!\overset{O}{\overset{\|}{C}}\!-\!L \qquad \text{Formula II}$$

wherein:

A is -H or amidino,

B is alkyl, cycloalkyl, cycloalkylalkyl, alkylcycloalkyl, alkylcycloalkylalkyl, aryl, aralkyl, alkylaryl, or alkylaralkyl, J is -H, alkyl, cycloalkyl, cycloalkylalkyl, alkylcycloalkyl, alkylcycloalkylalkyl, aryl, substituted aryl, aralkyl, substitued aralkyl, L is OR$^1$, or NR$^1$R$^2$, where R$^1$ and R$^2$ are independently -H, alkyl, cycloalkyl, cycloalkylalkyl, alkylcycloalkyl, alkylcycloalkylalkyl, aryl, aralkyl, alkylaryl, or alkylaralkyl, m is 1 to 5, n is 2 to 6, and p is 1 or 2;

or a pharmaceutically acceptable salt thereof.

A more preferred special embodiment of the present invention is described by the compounds of the special embodiment wherein A is -H, B is alkyl, cycloalkyl, cycloalkylalkyl, alkylcycloalkyl, alkylcycloalkylalkyl, J is -H, alkyl, cycloalkyl, cycloalkylalkyl, alkylcycloalkyl, or alkylcycloalkylalkyl, m is 3, and n is 3 or 4.

A most preferred special embodiment of the special invention is described by the compounds of the more preferred special embodiment wherein A is -H, B is alkyl, J is alkyl, cycloalkyl, or cycloalkylalkyl, R$^1$ and R$^2$ are independently -H, alkyl, cycloalkyl, cycloalkylalkyl, alkylcycloalkyl, alkylcycloalkylalkyl, m is 3, n is 3 or 4, and p is 1.

Representative compounds of the present invention include:

N-[N-[N-(4-(piperidin-4-yl)butanoyl)-N-ethylglycyl] aspartyl] valine,

N-[N-[N-(4-(piperidin-4-yl)butanoyl)-N-ethylglycyl] aspartyl]-D-valine,

N-[N-[N-(3-(piperidin-4-yl)propanoyl)-N-ethylglycyl] aspartyl] valine,

N-[N-[N-(5-(piperidin-4-yl)pentanoyl)-N-ethylglycyl] aspartyl] valine,

N-[N-[N-(4-(piperidin-4-yl)butanoyl)-N-ethylglycyl] aspartyl]-L-α-cyclohexyl glycine, N-[N-[N-(4-(piperidin-4-yl)butanoyl)-N-ethylglycyl] aspartyl]-β-cyclohexylalanine, N-[N-[N-(4-(piperidin-4-yl)butanoyl)-N-ethylglycyl] aspartyl] norleucine, N-[N-[N-(4-(piperidin-4-yl)butanoyl)-N-ethylglycyl] aspartyl]-L-α-(2,2-dimethyl)prop-3-yl glycine, N-[N-[N-(4-(piperidin-4-yl)butanoyl)-N-ethylglycyl]
aspartyl]-L-β-decahydronaphth-1-yl alanine, N-[N-[N-(4-(piperidin-4-yl)butanoyl)-N-ethylglycyl]
aspartyl]-L-α-(2-cyclohexylethyl)glycine, N-[N-[N-(4-(piperidin-4-yl)butanoyl)-N-ethylglycyl]
aspartyl] phenylalanine, N-[N-[N-(4-(piperidin-4-yl)butanoyl)-N-ethylglycyl]
aspartyl]-L-β-naphth-1-yl alanine, N-[N-[N-(4-(piperidin-4-yl)butanoyl)-N-ethylglycyl]
aspartyl]-L-β-naphth-2-yl alanine, N-[N-[N-(4-(piperidin-4-yl)butanoyl)-N-ethylglycyl]
aspartyl]-L-β-cyclohexyl alanine amide, N-[N-[N-(4-(piperidin-4-yl)butanoyl)-N-ethylglycyl]
aspartyl]-L-β-cyclohexyl alanine, ethyl ester, 2-cyclohexyl-N-[N-[N-(4-(piperidin-4-yl)butanoyl)-N-ethylglycyl]aspartyl]-ethylamine, N-[N-[N-(4-(piperidin-4-yl)butanoyl)-N-ethylglycyl]
aspartyl]-L-β-cis-decahydronaphth-2-ylalanine, 3-Adamant-1-ylpropyl-N-[N-(4-(piperidin-4-yl)butanoyl)-N-ethylglycyl]aspartate, N-[N-[N-(4-(piperidin-4-yl)butanoyl)-N-ethylglycyl]
aspartyl]-α-aminocyclohexanecarboxylic acid, N-[N-[N-(4-(piperidin-4-yl)butanoyl)-N-ethylglycyl]
aspartyl]-β-cyclohexyl-D-alanine, N-[N-[N-(4-(piperidin-4-yl)butanoyl)-N-ethylglycyl]
aspartyl]-β-decahydronaphth-1-ylalanine, N-[N-[N-(4-(piperidin-4-yl)butanoyl)-N-ethylglycyl]
aspartyl]-β-cyclohexylalanine ethyl amide, N-[N-[N-(4-(piperidin-4-yl)butanoyl)-N-ethylglycyl]
aspartyl]-β-cyclooctylaianine, N-[N-[N-(4-(piperidin-4-yl)butanoyl)-N-ethylglycyl]
aspartyl]-α-cyclohexylmethylethanolamine, N-[N-[N-(4-(piperidin-4-yl)butanoyl)-N-ethylglycyl]
aspartyl]-β-cyclohexylmethylalanine amide, N-[N-[N-(4-(piperidin-4-yl)butanoyl)-N-ethylglycyl]
aspartyl]-β-adamant-1-ylalanine, N-[N-[N-(4-(piperidin-4-yl)butanoyl)-N-ethylglycyl]
aspartyl]-β-(1,2,3,4)-tetrahydronaphth-5-ylalanine, N-[N-[N-(4-(piperidin-4-yl)butanoyl)-N-ethylglycyl]
aspartyl]-β-(4-cyclohexyl)cyclohexylalanine, N-[N-[N-(4-(piperidin-4-yl)butanoyl)-N-ethylglycyl]
aspartyl]-β-cycloheptylalanine, N-[N-[N-(4-(piperidin-4-yl)butanoyl)-N-ethylglycyl]
aspartyl]-β-cyclooctylalanine amide, N-[N-[N-(4-(piperidin-4-yl)butanoyl)-N-ethylglycyl]
aspartyl]-α-cyclohexylpropylglycine, N-[N-[N-(4-(piperidin-4-yl)butanoyl)-N-ethylglycyl]
aspartyl]-β-cyclooctylmethylalanine, N-[N-[N-(4-(piperidin-4-yl)butanoyl)-N-ethylglycyl]
aspartyl]-β-cyclopentylalanine, and N-[N-[N-(4-(piperidin-4-yl)butanoyl)-N-ethylglycyl]
aspartyl]-β-cyclohexylmethylalanine ethyl ester, and
pharmaceutically acceptable salts thereof.

Compounds of the present invention contain asymmetric centers. These asymmetric centers may independently be in either the R or S configuration. The present invention comprises the individual stereoisomers and mixtures thereof.

The compounds of the present invention may be useful in the form of the free base or acid or in the form of a pharmaceutically acceptable salt thereof. All forms are within the scope of the invention.

Where the compound of the present invention is substituted with a basic moiety, acid addition salts may be formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial antithrombotic properties inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, malonate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial antithrombotic properties inherent in the free acid are not vitiated by side effects ascribable to the cations. Pharmaceutically acceptable salts within the scope of the invention are those derived from the following bases: sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydroxide, carbonate or similar reactive compound of the chosen metal in an aqueous solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

Compounds of this invention may be prepared in accordance with the reaction sequences described below, or can be prepared by methods known in the art. The starting materials used in the preparation of compounds of this invention are known or are commercially available, or can be prepared by known methods or by specific reaction schemes described herein.

The compounds of the present invention may be readily prepared by standard solid phase or solution phase peptide synthesis procedures using starting materials and/or readily available intermediates from chemical supply companies such as Aldrich or Sigma, (H. Paulsen, G. Merz, V. Weichart, "Solid-Phase Synthesis of O-Glycopeptide Sequences", Angew. Chem. Int. Ed. Engl. 27 (1988); H. Mergler, R. Tanner, J. Gosteli, and P. Grogg, "Peptide Synthesis by a Combination of Solid-Phase and Solution Methods I: A New Very Acid-Labile Anchor Group for the Solid-Phase Synthesis of Fully Protected Fragments. Tetrahedron letters 29, 4005 (1988); Merrifield, R. B., "Solid Phase Peptide Synthesis after 25 Years: The Design and Synthesis of Antagonists of Glucagon", Makromol. Chem. Macromol. Symp. 19, 31 (1988)).

A preferred method of preparing compounds of the present invention is by the solution phase method depicted in Scheme I, below.

A', E', F', G', and R' are A, B, E, F, G, and R, respectively, or are protected analogues thereof, or precursor substituents thereto; and $P_1$, $P_2$, and $P_3$ are amino acid protecting groups.

The compounds of the present invention are available generally by initially coupling the appropriate amino acid or other appropriate Z group precursor, where Z is as defined hereinabove, which contains a free primary or secondary amine to the free carboxylic acid portion of a protected derivative of aspartic acid.

The functional groups of aspartic acid or any functional groups of the Z group precursor which are not to be coupled are protected where necessary by blocking groups to prevent cross reaction during the coupling procedure, as are the amino acid derivatives and azacycloalkylalkanoic acid derivatives used in subsequent synthetic steps. These blocking groups include N-α-tertiary butyloxycarbonyl (BOC), benzyloxycarbonyl (CBZ), benzyl, methyl, t-butyl, 9-fluorenylmethyloxycarbonyl (FMOC), 2-(trimethylsilyl) ethyl, and 4-methoxy-2,3,6-trimethylbenzenesulfonyl.

A preferred protected derivative of aspartic acid is BOC aspartic acid β-benzyl ester. Coupling is done by methods known in the art. A preferred method for carrying out the coupling is combining the amine and carboxylic acid in an appropriate aprotic organic solvent, for example methylene chloride or dimethylformamide (DMF), in the presence of appropriate coupling agents. A preferred coupling agent is isopropyl chloroformate in the presence of N-methylpiperidine. Another preferred coupling agent is 1-(3-dimethylaminopropyl)-3-ethylcarbodiimide hydrochloride (EDC) in the presence of 1-hydroxybenzotriazole (HOBT) and triethylamine. Still another preferred coupling agent is bis(2-oxo-3-oxazolidinyl)-phosphonic chloride (BOP-Cl) in the presence of triethylamine.

The resulting protected product is selectively deprotected by known methods to give the N-terminal free amine of the

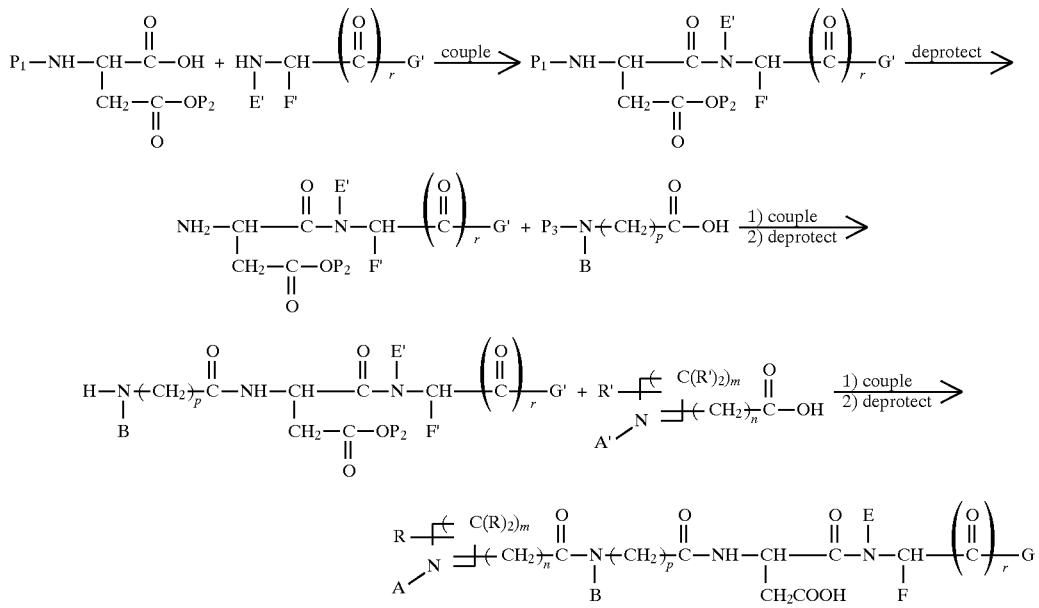

wherein A, B, E, F, G, R, m, n, p, and r are as defined hereinabove;

aspartic acid moiety. A preferred method for removing the BOC group is treatment with trifluoroacetic in an aprotic organic solvent, for example, methylene chloride.

The resulting deprotected product is then coupled with the appropriately N-protected N-substituted glycine or β-alanine derivative having a free carboxyl group. The resulting producted is then N-deprotected. The resulting free amine is then coupled with the appropriate protected azacycloalkylalkanoic acid and this product deprotected by known methods to give the final product.

In another preferred method, the compounds of the present invention may be prepared by solid phase methods well known in the art. In the solid method the C-terminal residue is bound at the carboxyl portion to an insoluble resin, for example the residue may be bound as a p-alkoxybenzyl alcohol resin ester. In a manner which is similar to the solution phase method the protected amino acid or other residues are added one at a time until the total sequence has been built up on the resin. The compound is then deprotected and released from the resin by standard methods to give the final compound.

During the preparation of compounds of the present invention, or intermediates thereto, it may also be desirable or necessary to prevent cross-reaction between chemically active substituents other than those present on naturally occuring or other amino acids. The substituents may be protected by standard blocking groups which may subsequently be removed or retained, as required, by known methods to afford the desired products or intermediates (see, for example, Green, "Protective Groups in Organic Synthesis", Wiley, N.Y., 1981). Selective protection or deprotection may also be necessary or desirable to allow conversion or removal of existing substituents, or to allow subsequent reaction to affort the final desired product.

The invention is further explained by the following illustrative examples. In the following examples, unless otherwise indicated, α-amino acids which have the possibility of having chiral α-carbons are in the L configuration.

Unless otherwise indicated, reported mass spectral analysis data are Low Resolution Fast Atom Bombardment performed on a VG 70SE with "calculated" values being $(M+H)^+$. Nuclear magnetic resonance spectral data is obtained on a Brucker ACF 300, in $D_2O$. Flash chromatography is done on silica gel. High performance liquid chromatography (HPLC) is done on a Dynamax 60 Å, 8μ C-18 Reverse Phase column.

EXAMPLE 1

N-[N-[N-(4-(piperidin-4-yl)butanoyl)-N-ethylglycyl] aspartyl]-β-cyclohexylalanine

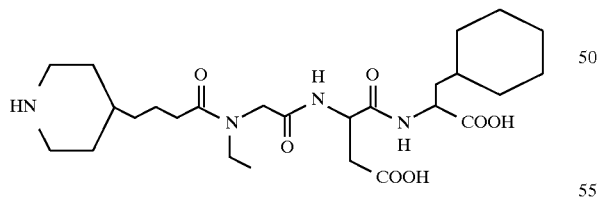

A. β-cyclohexylalanine (1.12 g) is dissolved in of methanol (50 ml) and hydrogen chloride gas is bubbled through the solution for about 15 minutes. The solution is evaporated in vacuo and toluene azeotroped from the residue to give β-cyclohexyl-L-alanine methyl ester as the hydrochloride salt.

B. BOC-L-aspartic acid β-benzyl ester (1.27 g) is dissolved in methylene chloride (20 ml). The solution is cooled to 0° C. and N-methyl piperidine (0.48 ml) is added followed by isopropyl chloroformate (3.94 ml). The solution is stirred at 0° C. for about two minutes and β-cyclohexyl-L-alanine methyl ester hydrochloride (0.88 g) is added. The solution is allowed to warm to room temperature and stirred overnight. The solution is evaporated in vacuo and the residue partitioned between ethyl acetate (200 ml) and 1N hydrochloric acid (HCl) (50 ml). The organic layer is washed with 1N HCl, saturated sodium bicarbonate solution, brine, dried over magnesium sulfate, filtered and evaporated in vacuo to give N-[BOC-L-aspartyl (β-benzyl ester)]-β-cyclohexyl-L-alanine, methyl ester.

C. N-[BOC-L-aspartyl (β-benzyl ester)]-β-cyclohexylalanine, methyl ester (2.01 g) is dissolved in methylene chloride (15 ml). The solution is cooled to 0° C. and trifluoroacetic acid (5 ml) is added over a period of about 1 minute. The solution is stirred at 0° C. for two hours, evaporated in vacuo and residue taken up into ethyl acetate and the organic solution washed with saturated sodium bicarbonate solution until the washes are basic. The organic solution is washed with brine, dried over magnesium sulfate, filtered and evaporated in vacuo to give L-aspartyl (β-benzyl ester)-β-cyclohexyl-L-alanine methyl ester.

D. Using essentially the coupling procedure of Example 1B, hereinabove, followed by essentially the deprotection procedure of Example 1C, hereinabove, N-ethylglycyl-L-aspartyl (β-benzyl ester)-L-β-cyclohexyl-L-alanine methyl ester is prepared from L-aspartyl (β-benzyl ester)-β-cyclohexyl-L-alanine methyl ester and N-BOC-N-ethylglycine.

E. 4-pyridine acetic acid (10 g) and platinum oxide (1.0 g) are combined in acetic acid (100 ml) and the mixture shaken under hydrogen at 50 psi for about 18 hours. The mixture is filtered and the solution evaporated in vacuo and toluene azeotroped from the residue to give 2-(piperidin-4-yl)acetic acid.

F. 2-(piperidin-4-yl)acetic acid (11.6 g) is dissolved in 1N aqueous sodium hydroxide solution (200 ml) and the solution cooled to 0° C. A solution of di-tert-butyl dicarbonate (18.0 g) in tetrahydofuran (THF) (100 ml) is added dropwise and the mixture allowed to warm to room temperature and stirred for about 18 hours. The mixture is evaporated in vacuo to remove THF and the residue is taken up into water and washed with ethyl acetate. Ethyl acetate is added to the aqueous layer and the mixture acidified with 1N HCl. The organic layer is separated and the aqueous layer extracted with ethyl acetate. The combined organic portions are washed with water, brine, dried over magnesium sulfate, filtered, and evaporated in vacuo to give N-BOC-2-(piperidin-4-yl)acetic acid.

G. N-BOC-2-(piperidin-4-yl)acetic acid (15.8 g) is dissolved in THF (150 ml) and 1M borane/THF (70 ml) is added dropwise. The solution is stirred at room temperature for about 20 hours and 1N sodium hydroxide solution (200 ml) is added dropwise. The THF is evaporated in vacuo and the aqueous residue extracted with ethyl acetate. The ethyl acetate solution is washed with water, dried over sodium sulfate, filtered, and evaporated in vacuo to give N-BOC-2-(piperidin-4-yl) ethanol.

H. A solution of oxalyl chloride (11.8 g) in methylene chloride (180 ml) is cooled to −78° C. and dimethyl sulfoxide (DMSO) (8.9 ml) is added dropwise. The solution is stirred at −78° C. for about 3 minutes and a solution of N-BOC-2-(piperidin-4-yl)ethanol (14.3 g) in methylene chloride (250 ml) is added over a period of about 10 minutes. The solution is stirred for about 1 hour and N-methyl morpholine (21.6 g) is added over a period of about 15 minutes. The solution is allowed to warm to room temperature and, after about 30 minutes, methyl (triphenylphosphoranylidene) acetate (68.6 g) is added. The solution is stirred at room temperature for about 18 hours, evaporated in vacuo and the residue taken up in ethyl acetate. The ethyl acetate solution is washed with water, 5% HCl, 5% sodium hypochlorite solution, water, brine, dried over sodium sulfate, filtered and evaporated in vacuo to give methyl 4-(N-BOC-piperidin-4-yl)trans-crotonate.

I. Methyl 4-(N-BOC-piperidin-4-yl)trans-crotonate (11.5 g) is dissolved in methanol (200 ml) and 10% palladium/carbon (3 g) is added and the mixture shaken under hydrogen at 50 psi for 18 hours. The mixture is filtered, fresh catalyst added to the solution, and hydrogenation repeated. The mixture is filtered and evaporated in vacuo to give methyl 4-(N-BOC-piperidin-4-yl) butyrate.

J. To a mixture of 1N aqueous sodium hydroxide (100 ml) and methanol (200 ml) is added methyl 4-(N-BOC-piperidin-4-yl) butyrate (10.1 g) and the mixture stirred at room temperature for about 18 hours. The mixture is evaporated in vacuo, diluted with water, and washed with ether. The aqueous portion is acidified with 5% HCl, extracted with ethyl acetate and the organic solution washed with water, brine, dried over sodium sulfate, filtered, and evaporated in vacuo to give 4-(N-BOC-piperidin-4-yl) butyric acid.

K. A solution of 4-(N-BOC-piperidin-4-yl) butyric acid (0.91 g) in methylene chloride (50 ml) is cooled to 0° C. and bis(2-oxo-3-oxazolidinyl)phosphinic chloride (BOP-Cl) (0.86 g) and triethylamine (0.47 ml) are added. The solution is stirred at 0° C. for about 10 minutes and N-ethylglycyl-L-aspartyl (β-benzyl ester) -L-β-cyclohexyl-L-alanine methyl ester (1.52 g) in a minimum of methylene chloride is added followed by dropwise addition of triethylamine (0.47 ml) in methylene chloride over a period of about 15 minutes. The mixture is stirred at 0° C. for about 1 hour, and at room temperature for about 18 hours. The mixture is evaporated in vacuo and the residue taken up into ethyl acetate. The organic solution is washed with 1N HCl, saturated sodium bicarbonate solution, brine, dried over magnesium sulfate, filtered,evaporated in vacuo and the residue purified by flash chromatography, eluting with 60% ethyl acetate in hexanes, to give N-[N-[N-(4-(N-BOC-piperidin-4-yl)butanoyl)-N-ethylglycyl]aspartyl(β-benzyl ester)]-β-cyclohexylalanine, methyl ester.

L. N-[N-[N-(4-(N-BOC-piperidin-4-yl)butanoyl)-N-ethylglycyl]aspartyl(β-benzyl ester)]-β-cyclohexylalanine, methyl ester (1.79 g) is dissolved in methanol (40 ml) and 10% palladium/carbon (0.25 g) is added. The mixture is shaken under hydrogen at 50 psi for about 18 hours. The mixture is filtered through a Celite pad and the filtrate evaporated in vacuo to give N-[N-[N-(4-(N-BOC-piperidin-4-yl)butanoyl)-N-ethylglycyl]aspartyl]-β-cyclohexylalanine, methyl ester. The ester is dissolved in methanol (20 ml) and 1N aqueous sodium hydroxide solution (10 ml) is added. The mixture is stirred at room temperature for about 4 hours, diluted with water (25 ml), and acidified to pH 2 with 1N HCl. The mixture is extracted with ethyl acetate (3×100 ml) and the ethyl acetate solution dried over magnesium sulfate, filtered and evaporated in vacuo to give N-[N-[N-(4-(N-BOC-piperidin-4-yl) butanoyl)-N-ethylglycyl]aspartyl]-β-cyclohexylalanine.

M. N-[N-[N-(4-(N-BOC-piperidin-4-yl)butanoyl)-N-ethylglycyl]aspartyl]-β-cyclohexylalanine (1.39 g) is dissolved in methylene chloride (15 ml) and the solution cooled to 0° C. Trifluoroacetic acid (5 ml) is added and the solution stirred at 0° C. for about 2.5 hours. The solution is evaporated in vacuo and the residue diluted with water, frozen, and lyophilized. The residue is purified by reverse phase HPLC, eluting with a gradient of 40% to 80% methanol in water, containing 0.1% trifluoroacetic. The appropriate fractions are combined, and lyophilized to give N-[N-[N-(4-(piperidin-4-yl) butanoyl)-N-ethylglycyl]aspartyl]-β-cyclohexylalanine as the trifluoroacetate salt. M.S., Calc'd: 525, Found: 525; NMR, δ=4.58–4.48 (m, 1H), 4.35–4.22 (m, 1H), 3.88 (s, 2H), 3.32 (q, 2H), 3.28–3.10 (m, 2H), 2.88–2.60 (m, 4H), 2.33 (t, 2H), 1.85–1.70 (m, 2H), 1.62–1.35 (m, 10H), 1.30–1.06 (m, 5H), 1.04–0.65 (m, 8H).

Using essentially the procedures of Example 1 above, the following compounds are prepared from the appropriate starting materials.

EXAMPLE 2

N-[N-[N-(4-(piperidin-4-yl)butanoyl)-N-ethylglycyl] aspartyl] valine

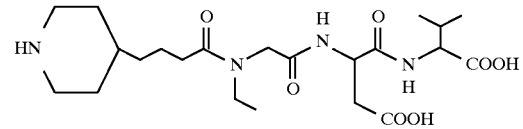

M.S., Calc'd: 471, Found: 471; NMR, δ=4.15–4.05 (m, 2H), 3.90 (s, 2H), 3.30 (q, 2H), 3.30–3.15 (m, 2H), 2.90–2.60 (m, 4H), 2.33 (t, 2H), 2.05 (q, 1H), 1.85–1.72 (m, 2H), 1.55–1.35 (m, 3H), 1.30–1.08 (m, 4H), 1.02 (t, 3H), 0.70 (d,6H).

EXAMPLE 3

N-[N-[N-(4-piperidin-4-yl)-N-ethylglycyl]aspartyl] phenylalanine H

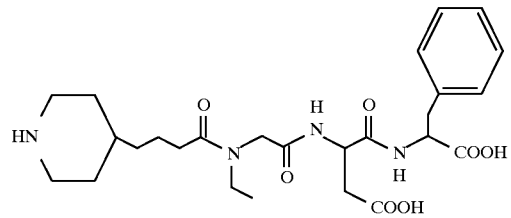

M.S., Calc'd: 519, Found: 519; NMR, δ=7.20–6.95 (m, 5H), 4.55–4.35 (m, 2H), 3.73 (s, 2H), 3.30–2.40 (m, 10H), 2.25 (t, 2H), 1.75–1.60 (m, 2H), 1.4–1.25 (m, 3H), 1.20–0.97 (m, 4H), 0.92 (t, 3H).

EXAMPLE 4
N-[N-[N-4-(piperidin-4-yl)butanoyl)-N-ethylclycyl]aspartyl]-D-valine

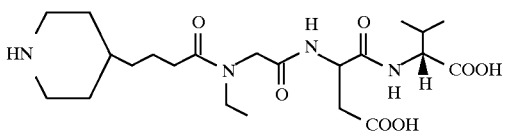

M.S., Calc'd: 471, Found: 471; NMR, δ=4.10–3.98 (m, 2H), 3.85 (s, 2H), 3.28 (q, 2H), 3.23–3.10 (m, 2H), 2,82–2.58 (m, 4H), 2.28 (t, 2H), 2.02 (q, 1H), 1.80–1.65 (m, 2H), 1.50–1.28 (m, 3H), 1.25–1.00 (m, 4H), 0.95 (t, 3H), 0.78–0.65 (m, 6H).

EXAMPLE 5
N-[N-[N-(4-(piperidin-4-yl)butanoyl)-N-ethylglycyl]aspartyl]-L-α-2,2-dimethyl)prop3-yl glycine

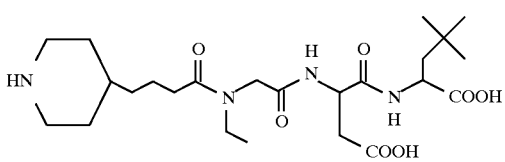

M.S., Calc'd: 499, Found: 499; NMR, δ=4.63–4.55 (m, 1H), 4.30–4.20 (m, 1H), 3.88 (s, 2H), 3.33 (q, 2H), 3.30–3.15 (m, 2H), 2.88–2.60 (m, 4H), 2.35 (t, 2H), 1.85–1.75 (m, 2H), 1.73–1.35 (m, 5H), 1.30–1.08 (m, 4H), 1.03 (t, 3H), 0.78 (s, 9H).

EXAMPLE 6
N-[N-[N-(4-piperidin-4-yl)butanoyl)-N-ethylglycyl]aspartyl]norleucine

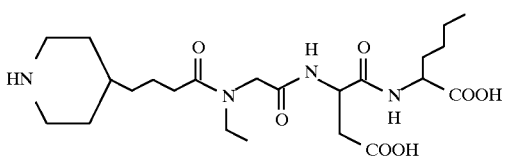

M.S., Calc'd: 485, Found: 485; NMR, δ=4.58–4.50 (m, 1H), 4.20–4.10 (m, 1H), 3.85 (s, 2H), 3.32 (q, 2H), 3.25–3.10 (m, 2H), 2.85–2.55 (m, 4H), 2.3 (t, 2H), 1.82–1.50 (m, 4H), 1.50–1.30 (m, 3H), 1.28–1.05 (m, 8H), 0.98 (t, 3H), 0.75–0.60 (m, 3H).

EXAMPLE 7
N-[N-[N-(4-(piperidin-4-yl)butanoyl)-N-ethylglycyl]aspartyl]-L-β-naphth-1-yl alanine

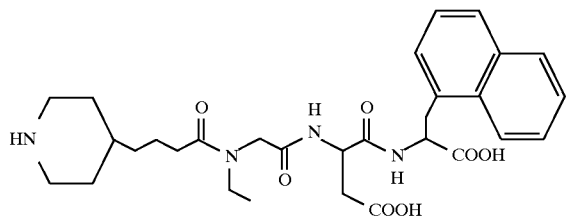

M.S., Calc'd: 569, Found: 569; NMR, δ=8.00–7.15 (m, 7H), 4.60–4.45 (m, 2H), 3.71 (s, 2H), 3.65–3.50 (m, 2H), 3.40–2.98 (m, 4H), 2.70–2.42 (m, 4H), 2.21 (t, 2H), 1.70–1.45 (m, 2H), 1.40–0.96 (m, 7H), 0.92 (t, 3H).

EXAMPLE 8

N-[N-[N-(4(piperidin-4-yl)butanoyl)-N-ethylglycyl]aspartyl]-L-β-naphth-2-yl alanine

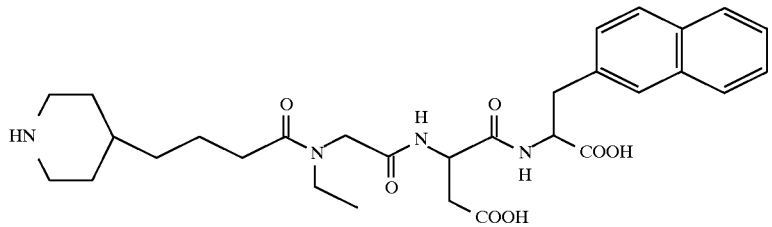

M.S., Calc'd: 569, Found: 569; NMR, δ=7.65–7.03 (m, 7H), 4.60–4.45 (m, 2H), 3.41 (s, 2H), 3.20–3.01 (m, 3H), 3.00–2.71 (m, 3H), 2.68–2.40 (m, 4H), (t, 2H), 1.68–1.42 (m, 3H), 1.25–0.85 (m, 6H), 0.71 (t, 3H).

EXAMPLE 9
N-[N-[N-(3-(piperidin-4-yl)propanoyol)-N-ethylglycyl]aspartyl] valine

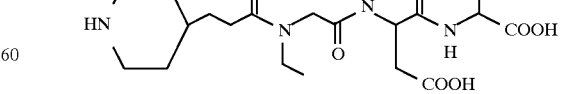

M.S., Calc'd: 547, Found: 457; NMR, δ=4.62 (m, 2H), 3.90 (s, 2H), 3.33 (m, 4H), 2.66 (m, 4H), 2.37 (t, 2H), 2.16 (m, 1H), 2.03 (m, 1H), 1.78 (m, 2H), 1.44 (m, 2H), 1.20 (m, 2H), 1.00 (m, 3H), 0.78 (d, 6H).

EXAMPLE 10
N-[N-[N-(5-(piperidin-4-yl)pentanoyl)-N-ethylglycyl] aspartyl] valine

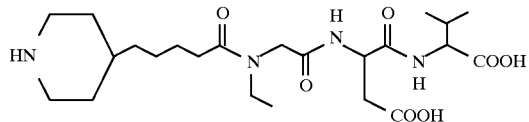

M.S., Calc'd: 485, Found: 485; NMR, δ=4.20–4.05 (m, 2H), 3.92 (s, 2H), 3.33 (m, 2H), 3.28–3.15 (m, 2H), 2.90–2.61 (m, 4H), 2.34 (t, 2H), 2.06 (m, 1H), 1.85–1.70 (m, 2H), 1.55–1.32 (m, 3H), 1.30–1.12 (m, 6H), 1.06 (t, 3H), 0.81 (d, 6H).

EXAMPLE 11
N-[N-[N-(4-(piperidin-4-yl)butanoyl)-N-ethylglycyl] aspartyl]-L-β-cyclohexyl alanine, ethyl ester

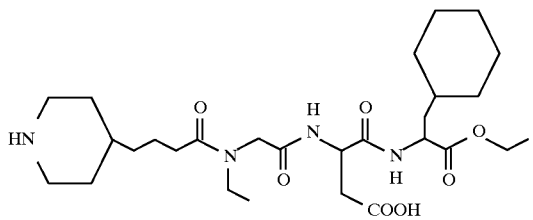

A. β-cyclohexyl alanine (1.5 g) is dissolved in absolute ethanol (75 ml) and the solution cooled to 0° C. Thionyl chloride (1.1 ml) is added dropwise over a period of 10–15 minutes, the solution allowed to warm to room temperature, and then stirred at room temperature for about 18 hours. The reaction mixture is evaporated in vacuo, toluene is azeotroped twice from the residue, and the residue is taken up into ethyl acetate. The ethyl acetate solution is washed with water, 1N sodium hydroxide, water, brine, dried over sodium sulfate, filtered, and evaporated in vacuo to give β-cyclohexyl alanine, ethyl ester.

B. Using essentially the procedures of Examples 1B through 1M (eliminating the aqueous sodium hydroxide hydrolysis of step 1L) gives the desired product.

M.S., Calc'd: 553, Found: 553; NMR, δ=4.4 (1H, m); 4.1 (4H, q); 4.0 (2H, d; 3.2–3.5 (5H, m); 2.7–3.0 (5H, m); 2.4 (2H, t); 2.2 (1H, m); 1.9 (2H, d); 1.4–1.7 (7H, m); 0.7–1.4 (18H, m).

EXAMPLE 12
N-[N-[N-(4-(piperidin-4-yl)butanoyl)-N-ethylglycyl] aspartyl]-L-β-cyclohexyl alanine amide

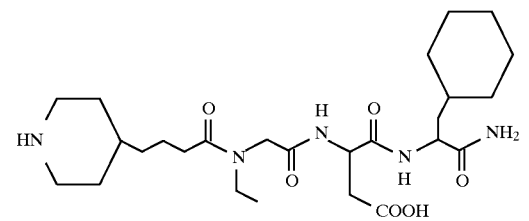

A. N-BOC-β-cyclohexylalanine (2.0 g.) and triethyl amine (1.03 ml) are dissolved together in THF (100 ml) and the solution cooled to −20° C. Isobutyl chloroformate (1.06 ml) is added and the solution stirred at −20° C. for about 30 minutes. A saturated solution of ammonia in methanol (20 ml) is added and the solution allowed to warm to room temperature and stirred at room temperature for about 18 hours. The solution is evaporated in vacuo and the residue dissolved in ethyl acetate. The ethyl acetate solution is washed with water, 5% HCl, saturated sodium bicarbonate solution, water, brine, dried over sodium sulfate, filtered and evaporated in vacuo to give N-BOC-β-cyclohexylalanine amide.

B. N-BOC-β-cyclohexylalanine amide (2.0 g.) is dissolved in ethyl acetate (100 ml) and HCl gas is bubbled through the solution and the solution stirred at room temperature for about 18 hours. The solution is evaporated in vacuo and toluene azeotroped twice from the residue to give β-cyclohexylalanine amide as the hydrochloride.

C. Using essentially the procedures of Example 1B thru 1M (eliminating the aqueous sodium hydroxide hydrolysis of Example 1L) gives the desired product.

M.S., Calc'd: 524, Found: 524; NMR, δ=8.4 (1H, d); 8.1 (1H, d); 4.2 (2H, q); 4.1 (1H, s); 3.9 (4H, q); 3.4 (2H, q); 3.3 (4H, d); 2.8–3.0 (6H, m); 2.4 (2H, t); 2.2 (1H, m); 1.8 (4H, d); 1.4–1.7 (7H, m); 0.7–1.3 (10H, m).

EXAMPLE 13
N-[N-[N-(4-(piperidin-4-yl)butanoyl)-N-ethylglycyl] aspartyl]-L-α-cyclohexyl glycine

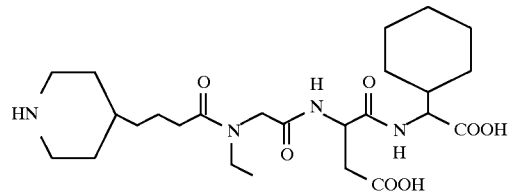

A. A solution of α-phenylglycine, methyl ester, hydrochloride salt (1.0 g) in THF (25 ml) is cooled to 0° C. and triethylamine (1.38 ml) is added. To this mixture is added a solution of di-tert-butyl dicarbonate (1.08 g) in THF (25 ml), and the mixture allowed to warm to room temperature and stirred at room temperature for about 18 hours. The solution is evaporated and the residue taken up into ethyl acetate (200 ml) and the organic solution washed with 1N HCl, saturated sodium bicarbonate solution, brine, dried over magnesium sulfate, filtered, and evaporated in vacuo to give N-BOC-α-phenylglycine, methyl ester.

B. N-BOC-α-phenylglycine, methyl ester (1.2 g) is dissolved in methanol (50 ml) containing acetic acid (1 ml). 5% rhodium on aluminum powder (0.60 g) is added and the mixture shaken under 50 psi hydrogen for about 18 hours. The mixture is filtered, evaporated in vacuo, and the residue taken up into ethyl acetate. The organic solution is washed with water, saturated sodium bicarbonate solution, water, brine, dried over magnesium sulfate, filtered, evaporated in vacuo to give N-BOC-α-cyclohexylglycine, methyl ester.

C. Using essentially the procedures of Examples 1B–1M, the desired product is obtained.

M.S., Calc'd: 511, Found: 511; NMR, δ=4.62–4.55 (1H, m); 4.06 (2H, m); 3.85 (2H, s); 3.30 (2H, q); 3.23–3.10 (2H, m); 2.85–2.55 (4H, m); 2.30 (2H, t); 1.83–1.60 (3H, m), 1.59–1.32 (8H, m); 1.30–0.75 (12H, m).

EXAMPLE 14
N-[N-[N-(4-(piperidin-4-yl)butanoyl)-N-ethylglycyl]
aspartyl]-L-β-decahydronaphth-1-yl alanine

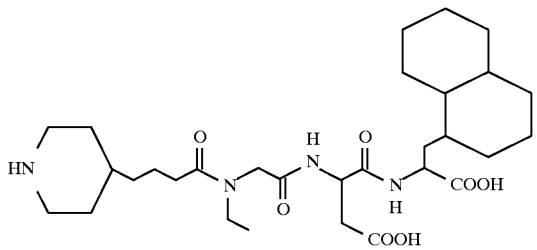

A. β-(1-naphthyl)alanine (2.0 g) is stirred in a saturated hydrogen chloride/methanol solution for about 2 hours at room temperature. The mixture is evaporated in vacuo and toluene azeotroped twice from the residue. The residue is suspended in methylene chloride, N-methyl morpholine (1.02 ml) added, and the mixture cooled to 0° C. Di-tert-butyl dicarbonate (2.02 g) and 4-dimethylaminopyridine (DMAP) (0.8 g) are added, the solution allowed to warm to room temperature, and stirred at room temperature for about 2 hours. The mixture is washed with 5% HCl, water, dried over sodium sulfate, filtered, and evaporated in vacuo to give N-BOC-β-(1-naphthyl)alanine, methyl ester.

B. N-BOC-β-(1-naphthyl)alanine, methyl ester (2.0 g) and 5% rhodium on alumina (1.0 g) are combined in methanol (50 ml) containing acetic acid (1.0 ml) and the mixture shaken under hydrogen at 50 psi for about 18 hours. The mixture is filtered, evaporated in vacuo, and the residue taken up into ethyl acetate. The organic solution is washed with water, 5% sodium bicarbonate solution, water, brine, dried over sodium sulfate, filtered, and evaporated in vacuo to give L-β-decahydronaphth-1-yl alanine, methyl ester.

C. Using essentially the procedures of Examples 1B through 1M, the desired product is obtained.
M.S., Calc'd: 579, Found: 579; NMR, δ=4.1–4.3 (m, 1H), 3.8–4.1 (m, 2H), 2.6–2.9 (m, 4H), 2.3 (m, 1H), 2.0 (m, 1H), 1.8 (d, 3H), 0.5–1.6 (m, 33H),

EXAMPLE 15
2-cyclohexyl-N-[N-[N-(4-(piperidin-4-yl)butanoyl)-N-ethylglycyl]aspartyl]-ethylamine

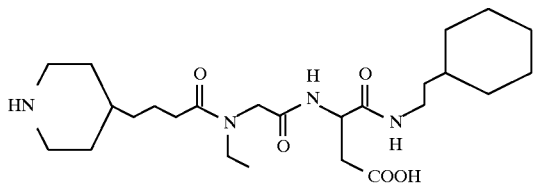

A. 2-phenylethylamine (2.0 g) is dissolved in methylene chloride and the solution cooled to 0° C. Di-tert-butyl dicarbonate (4.0 g) and DMAP (0.4 g) are added. The solution is allowed to warm to room temperature and stirred at room temperature for about 18 hours. The solution is washed with 5% HCl, water, filtered and evaporated in vacuo to give N-BOC-2-phenylethylamine.

B. N-BOC-2-phenylethylamine (3.1 g) and 5% rhodium on alumina (1.1 g) are combined in methanol (40 ml) containing acetic acid (1.0 ml). The mixture is shaken under hydrogen at 50 psi for about 20 hours. The mixture is filtered, evaporated in vacuo, and the residue taken up into ethyl acetate. The organic solution is washed with water, 5% sodium bicarbonate solution, water, brine, dried over sodium sulfate, filtered, and evaporated in vacuo to give N-BOC-2-cyclohexylethylamine.

C. Using essentially the procedures of Examples 1B through 1M (eliminating the aqueous sodium hydroxide hydrolysis of Example 1L), the desired product is obtained.
M.S., Calc'd: 481, Found: 481; NMR, δ=3.9 (s, 2H), 3.35 (d, 4H), 3.25 (d, 4H), 2.6–2.9 (m, 8H), 2.35 (t, 2H), 2.15 (t, 1H), 1.8 (4H, d), 1,4–1.7 (m, 7H), 0.9–1.3 (m, 12H), 0.7 (t, 2H).

EXAMPLE 16
N-[N-[N-(4-(piperidin-4-yl)butanoyl)-N-ethylglycyl]aspartyl]-L-α-(2-cyclohexylethyl)glycine

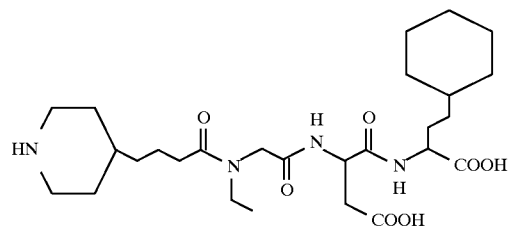

A. Using essentially the procedures of Example 13A, above, N-BOC-α-(2-phenylethyl)glycine, methyl ester is prepared from L-homophenylalanine.

B. Using essentially the procedure of Example 14B, above, N-BOC-α-(2-cyclohexylethyl)glycine, methyl ester is prepared from N-BOC-α-(2-phenylethyl)glycine, methyl ester.

C. Using essentially the procedures of Examples 1B through 1M, the desired product is obtained.
M.S., Calc'd: 539, Found: 539; NMR, δ=4.60–4.55 (m, 1H), 4.20–4.08 (m, 1H), 3.85 (s, 2H), 3.29 (q, 2H), 3.25–3.12 (m, 2H), 2.84–2.55 (m, 4H), 2.29 (t, 2H), 1.83–1.65 (m, 2H), 1.63–1.32 (m, 10H), 1.28–0.81 (m, 13H), 0.79–0.56 (m, 2H).

Using essentially the procedures of the above Examples, the following compounds are prepared from the appropriate starting materials.

EXAMPLE 17
N-[N-[N-(4-(piperidin-4-yl)butanoyl)-N-ethylglycyl]aspartyl]-L-β-cis-decahydronaphth-2-ylalanine

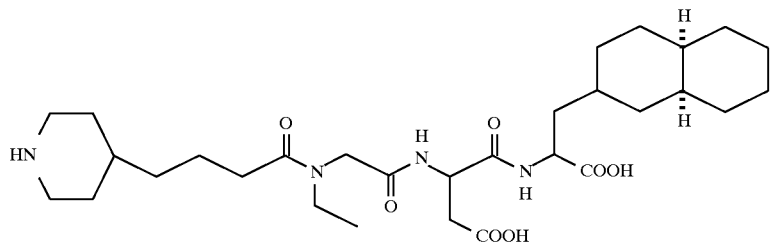

M.S., Calc'd: 579, Found: 579; NMR, δ=4.7 (m, 1H), 4.3 (m, 1H), 4.1 (d, 2H), 3.3–3.7 (m, 5H), 2.6–2.8 (m, 5H), 2.5 (t, 2H), 2.3 (t, 1H), 1.9 (d, 2H), 1.3–1.8 (m, 14H), 0.9–1.3 (m, 14H), 0.7–0.8 (m, 3H).

EXAMPLE 18
3-Adamant-1-ylpropyl-N-[N-(4-(piperidin-4-yl)butanoyl)-N-ethylglycyl]aspartate

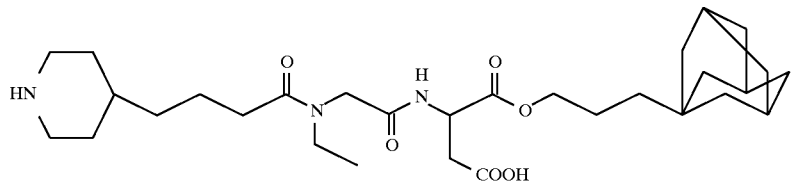

M.S., Calc'd: 548, Found: 548; NMR (DMSO-d$_6$), δ=4.65–4.50 (m, 1H), 4.05–3.85 (m, 4H), 3.35–3.15 (m, 4H), 2.90–2.50 (m, 4H), 2.30 (1, 2H), 2.18 (t, 1H), 1.94 (d, 2H), 1.85–1.35 (m, 20H), 1.32–1.12 (m, 4H), 1.10–0.90 (m, 5H).

EXAMPLE 19
N-[N-[N-(4-(piperidin-4-yl)butanoyl)-N-ethylglycyl]aspartyl]-α-aminocyclohexanecarboxylic acid

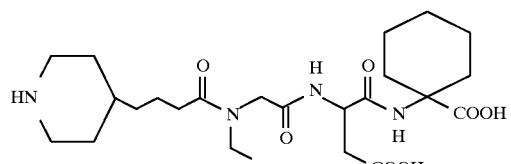

M.S., Calc'd: 497, Found: 497; NMR, δ=4.60–4.55 (m, 1H), 4.05 (s, 1H), 3.90 (s, 1H), 3.30 (q, 2H), 3.25–3.12 (m, 2H), 2.85–2.55 (m, 4H), 2.35 (t, 1H), 2.11 (t, 1H), 1.90–1.70 (m, 4H), 1.68–1.55 (m, 2H), 1.53–1.32 (m, 6H), 1.30–1.06 (m, 7H), 1.05–1.85 (m, 3H).

EXAMPLE 20
N-[N-[N-(4-(piperidin-4-yl)butanoyl)-N-ethylglycyl]aspartyl]-β-cyclohexyl-D-alanine

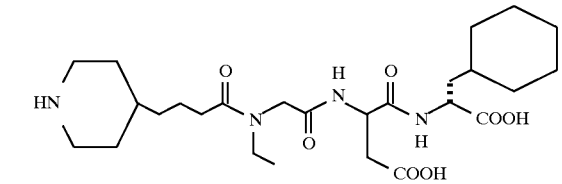

M.S., Calc'd: 525, Found: 525; NMR, δ=4.60–4.55 (m, 1H), 4.32–4.20 (m, 1H), 4.05 (s, 1H), 3.85 (s, 1H), 3.32 (q, 2H), 3.25–3.12 (m, 2H), 2.85–2.60 (m, 4H), 2.32 (t, 1H), 2.12 (t, 1H), 1.85–1.68 (m, 2H), 1.60–1.32 (m, 10H), 1.28–0.60 (m, 13H).

EXAMPLE 21
N-[N-[N-(4-(piperidin-4-yl)butanoyl)-N-ethylglycyl]aspartyl]-β-decahydronaphth-1-ylalanine

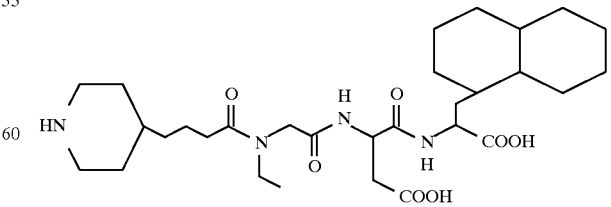

M.S., Calc'd: 579, Found: 579; NMR, δ=4.1–4.3 (1H, m), 3.8–4.1 (2H, m), 3.1–3.4 (4H, m), 2.6–2.9 (4H, m), 2.3 (1H, m), 2.0 (1H, m), 1.8 (3H, d), 0.5–1.6 (33H, m).

EXAMPLE 22
N-[N-[N-(4-(piperidin-4-yl)butanoyl)-N-ethylglycyl]aspartyl]-β-cyclohexylalanine ethyl amide

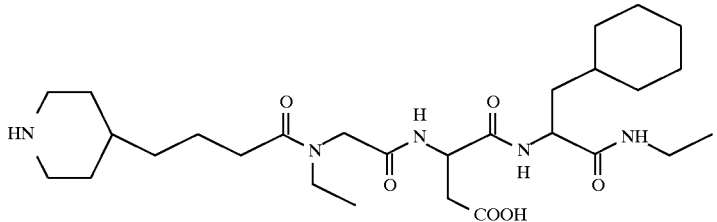

M.S., Calc'd: 552, Found: 552; NMR, δ=4.55–4.45 (m, 1H), 4.20–4.06 (m, 1H), 4.05–3.85 (m, 2H), 3.40–3.25 (m, 2H), 3.28–3.15 (m, 2H), 3.10–2.90 (m, 2H), 2.88–2.55 (m, 4H), 2.40–2.25 (m, 1H), 2.20–2.05 (m, 1H), 1.85–1.70 (m, 2H), 1.60–1.32 (m, 9H), 1.30–0.62 (m, 17H).

EXAMPLE 23
N-[N-[N-(4-(piperidin-4-yl)butanoyl)-N-ethylglycyl]aspartyl]-β-cyclooctylalanine

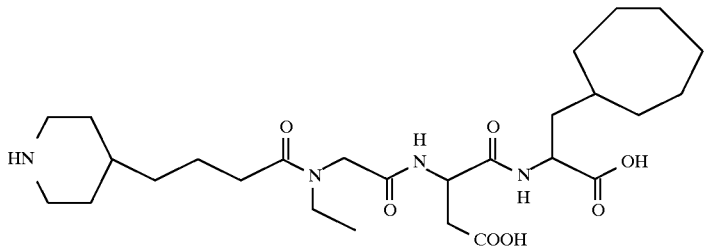

M.S., Calc'd: 553, Found: 553; NMR, δ=4.1–4.3 (1H, m), 3.8–4.1 (2H, m), 3.1–3.4 (4H, m), 2.6–2.9 (4H, m), 2.3 (1H, m), 2.0 (1H, m), 1.8 (2H, d), 0.5–1.6 (31H, m).

EXAMPLE 24
N-[N-[N-(4-(piperidin-4-yl)butanoyl)-N-ethylglycyl]aspartyl]-α-cyclohexylmethylethanolamine

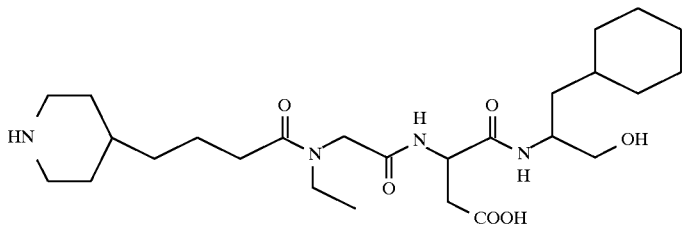

M.S., Calc'd: 511, Found: 511; NMR, δ=4.60–4.45 (m, 1H), 4.10–3.75 (m, 3H), 3.45–3.15 (m, 6H), 2.90–2.60 (m, 4H), 2.35 (t, 1H), 2.00–2.08 (m, 1H), 1.88–1.75 (m, 2H), 1.62–1.35 (m, 8H), 1.30–1.08 (m, 7H), 1.10–0.60 (m, 8H).

EXAMPLE 25
N-[N-[N-(4-(piperidin-4-yl)butanoyl)-N-ethylglycyl]aspartyl]-β-cyclohexylmethylalanine amide

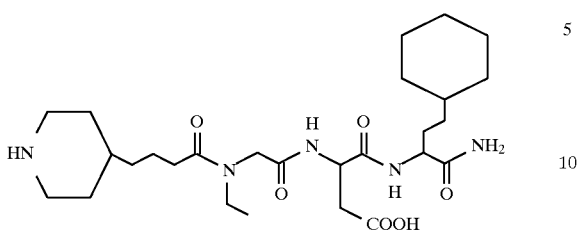

M.S., Calc'd: 538, Found: 538; NMR, δ=4.60–4.50 (m, 1H), 4.15–4.00 (m, 1H), 4.00–3.80 (m, 2H), 3.35 (q, 2H), 3.30–3.15 (m, 2H), 2.90–2.62 (m, 4H), 2.35 (t, 1H), 2.15 (t, 1H), 1.88–1.75 (m, 2H), 1.65–1.40 (m, 9H), 1.30–0.88 (m, 14H), 0.85–0.65 (m, 2H).

EXAMPLE 26
N-[N-[N-(4-(piperidin-4-yl)butanoyl)-N-ethylglycyl]aspartyl]-β-adamant-1-ylalanine

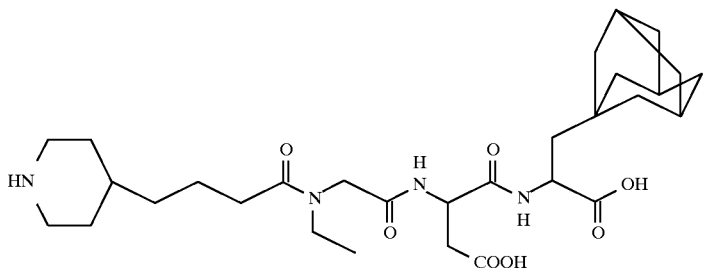

M.S., Calc'd: 577, Found: 577; NMR, δ=4.5–4.1 (1H, m), 4.1–4.2 (1H, m), 3.8 (2H, d), 3.2 (2H, q), 3.1–3.1 (6H, m), 2.4–2.98 (5H, m), 2.3 (1H, m), 2.0 (1H, m), 1.8 (4H, m), 1.2–1.7 (16H, m), 1.0–1.2 (6H, m), 0.8–1.0 (3H, m).

EXAMPLE 27
N-[N-[N-(4-(piperidin-4-yl)butanoyl)-N-ethylglycyl]aspartyl]-β-(1,2,3,4)-tetrahydronaphth-5-ylalanine

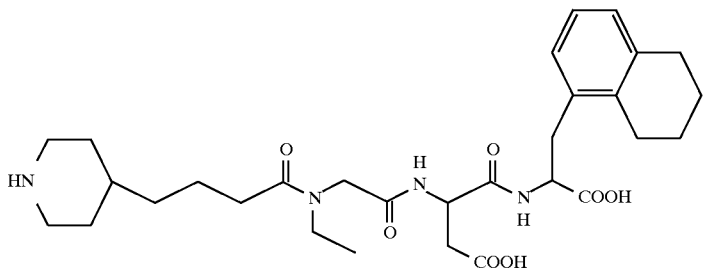

M.S., Calc'd: 573, Found: 573; NMR, δ=6.9 (d, 4H), 4.7 (m, 1H), 4.3 (m, 1H), 4.1 (d, 2H), 3.3–3.7 (m, 6H), 2.6–3.1 (m, 12H), 2.5 (t, 2H), 2.3 (t, 1H), 1.9 (d, 2H), 1.2–1.8 (m, 16H), 1.1 (t, 2H), 1.0 (t, 2H).

EXAMPLE 28
N-[N-[N-(4-(piperidin-4-yl)butanoyl)-N-ethylglycyl]aspartyl]-β-(4-cyclohexyl)cyclohexylalanine

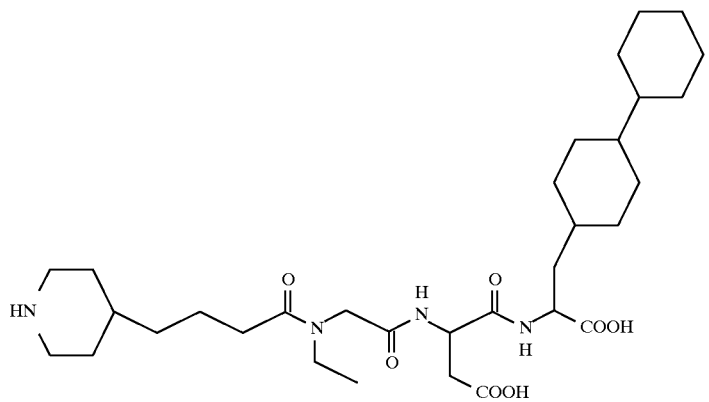
M.S., Calc'd: 607, Found: 607; NMR, δ=4.2–4.3 (1H, m), 3.9–4.1 (2H, m), 3.1–3.4 (5H, m), 2.6–2.9 (5H, m), 2.3 (1H, m), 2.0 (1H, m), 1.8 (3H, d), 0.9–1.6 (32H, m), 0.7–0.8 (3H, m).
H-1e), 2.65 (dd, 2H, H-13), 2.25 (t, 2H, H-8), 1.85–1.10 (m, 26H, H-3 through H-7 and H-15 through H-23), 1.06 (t, 3H, H-10).
EXAMPLE 29
N-[N-[N-(4-(piperidin-4-yl)butanoyl)-N-ethylglycyl]aspartyl]-β-cycloheptylalanine
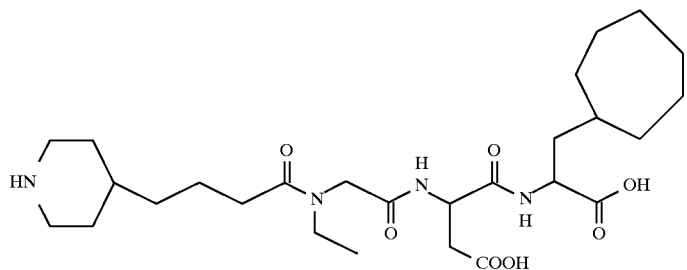
M.S., Calc'd: 539, Found: 539; NMR, δ=4.60–4.55 (m, 1H), 4.35–4.25 (m, 1H), 4.08 (S, 1H), 3.92 (S, 1H), 3.35 (q, 2H), 3.33–3.20 (m, 2H), 2.90–2.60 (m, 4H), 2.35 (t, 1H), 2.18 (t, 1H), 1.90–1.75 (m, 2H), 1.70–1.10 (m, 22H), 1.10–0.85 (m, 3H).
EXAMPLE 30
N-[N-[N-(4-(piperidin-4-yl)butanoyl)-N-ethylglycyl]aspartyl]-β-cyclooctylalanine amide
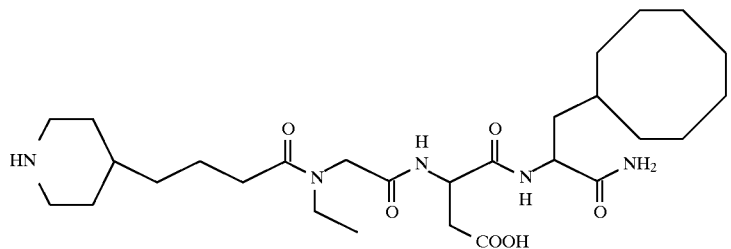
M.S., Calc'd: 551, Found: 551; NMR, δ=4.45 (dd, 1H, H-12), 4.18 (m, 1H, H-14), 3.89 (d, 1H, H-11), 3.69 (d, 1H, H-11), 3.31 (q, 2H, H-9), 3.18 (dt, 2H, H-1a), 2.74 (dt, 2H,

EXAMPLE 31
N-[N-[N-(4-(piperidin-4-yl)butanoyl)-N-ethylglycyl]aspartyl]-α-cyclohexylpropylglycine

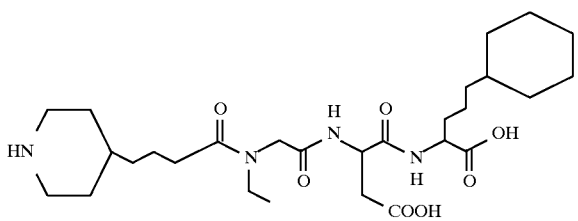

M.S., Calc'd: 553, Found: 553; NMR, δ=4.70–4.60 (m, 1H), 4.30–4.15 (m, 1H), 4.10 (S, 1H), 3.95 (S, 1H), 3.35 (q, 2H), 3.35–3.20 (m, 2H), 2.90–2.60 (m, 4H), 2.40 (t, 1H), 2.15 (t, 1H), 1.90–1.75 (m, 2H), 1.75–1.45 (m, 10H), 1.35–1.15 (m, 6H), 1.12–0.90 (m, 9H), 0.85–0.60 (m, 2H).

EXAMPLE 32
N-[N-[N-(4-(piperidin-4-yl)butanoyl)-N-ethylglycyl]aspartyl]-β-cyclooctylmethylalanine

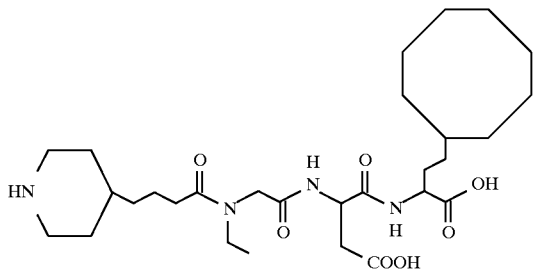

M.S., Calc'd: 567, Found: 567; NMR, δ=4.05–4.15 (m, 1H, 14), 3.75–4.00 (m, 2H, 11 & 18), 3.10–3.30 (m, 4H, 19 & 26 eq), 2.50–2.80 (m, 4H, 15 & 26 ax), 2.05–2.25 (m, 2H, 21), 0.75–1.75 (m, 31H, 1–10, 20 & 22–25).

EXAMPLE 33
N-[N-[N-(4-(piperidin-4-yl)butanoyl)-N-ethylglycyl]aspartyl]-β-cyclopentylalanine

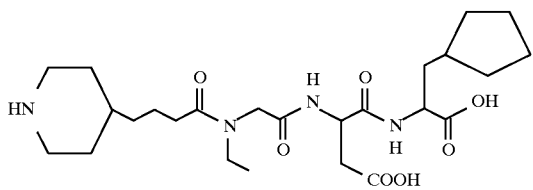

M.S., Calc'd: 511, Found: 511; NMR, δ=4.7 (m, 1H), 4.3 (m, 1H), 4.1 (d, 2H), 3.3–3.7 (m, 5H), 2.8 (t, 2H), 2.7 (m, 3H), 2.5 (t, 2H), 2.3 (t, 1H), 1.9 (d, 2H), 1.0–1.8 (m, 16H).

EXAMPLE 34
N-[N-[N-(4-(piperidin-4-yl)butanoyl)-N-ethylglycyl]aspartyl]-β-cyclohexylmethylalanine ethyl ester

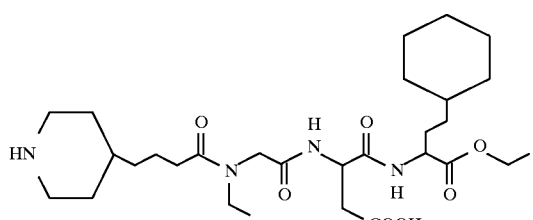

M.S., Calc'd: 567, Found: 567; NMR, δ=4.30–4.10 (m, 1H), 4.10–3.80 (m, 3H), 3.35 (q, 2H), 3.30–3.15 (m, 2H), 2.90–2.60 (m, 4H), 2.40–2.10 (t, 2H), 1.90–1.70 (m, 2H), 1.65–1.40 (m, 10H), 1.35–0.85 (m, 18H), 0.85–0.60 (m, 2H).

Compounds within the scope of the present invention inhibit platelet aggregation by inhibiting fibrinogen binding to activated platelets and other adhesive glycoproteins involved in platelet aggregation and blood clotting and are useful in the prevention and treatment of thrombosis associated with certain disease states, such as myocardial infarction, stroke, peripheral arterial disease and disseminated intravascular coagulation in humans and other mammals.

The compounds of this invention can normally be administered orally or parenterally, in the treatment or prevention of thrombosis associated disease states.

The compounds of this invention may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of platelet aggregation and thrombus inhibiting compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, they are suitably buffered, they are made isotonic with sufficient saline or glucose and sterilized by heating or microfiltration.

The dosage regimen in carrying out the method of this invention is that which insures maximum therapeutic response until improvement is obtained and thereafter the minimum effective level which gives relief. In general, the oral dose may be between about 0.1 mg/kg and about 100 mg/kg, preferably between about 0.1 mg/kg to 20 mg/kg, and most preferably between about 1 mg/kg and 20 mg/kg, and the i.v. dose about 0.1 µg/kg to about 100 µg/kg, preferably between about 0.1 µg/kg to 50 µg/kg, bearing in mind, of course, that in selecting the appropriate dosage in any specific case, consideration must be given to the patient's weight, general health, age, and other factors which may influence response to the drug. The drug may be administered orally 1 to 4 times per day, preferably once to twice daily.

The following pharmacologic tests evaluate the inhibitory activity of compounds of the present invention on fibrinogen-mediated platelet aggregation, fibrinogen binding to thrombin-stimulated platelets, and inhibition of ADP-induced ex-vivo platelet aggregation, and results of these tests correlate to the in-vivo inhibitory properties of compounds of the present invention.

The Platelet Aggregation Assay is based on that described in *Blood* 66 (4), 946–952 (1985). The Fibrinogen-Binding Assay is essentially that of Ruggeri, Z. M., et al., *Proc. Natl. Acad. Sci. USA* 83, 5708–5712 (1986) and Plow, E. F., et al., *Proc. Natl. Acad. Sci., USA* 82, 8057–8061 (1985). The Inhibition of ADP-Induced ex-vivo Platelet Aggregation assay is based on that of Zucker, "Platelet Aggregation Measured by the Photoelectric Method", *Methods in Enzymology* 169, 117–133 (1989).

Platelet Aggregation Assay

Preparation of Fixed-Activated Platelets

Platelets are isolated from human platelet concentrates using the gel-filtration technique as described by Marguerie, G. A., et al., *J. Biol. Chem.* 254, 5357–5363 (1979) and Ruggeri, Z. M., et al., *J. Clin. Invest.* 72, 1–12 (1983). The platelets are suspended at a concentration of $2 \times 10^8$ cells/ml in a modified calcium-free Tyrode's buffer containing 127 mM sodium chloride, 2 mM magnesium chloride, 0.42 mM $Na_2HPO_4$, 11.9 mM $NaHCO_3$, 2.9 mM KCl, 5.5 mM glucose, 10 mM HEPES, at a pH of 7.35 and 0.35% human serum albumin (HSA). These washed platelets are activated by addition of human α-thrombin at a final concentration of 2 units/ml, followed by thrombin inhibitor I2581 at a final concentration of 40 µM. To the activated platelets is added paraformaldehyde to a final concentration of 0.50% and this incubated at room temperature for 30 minutes. The fixed activated platelets are then collected by centrifugation at 650×g for 15 minutes. The platelet pellets are washed four times with the above Tyrode's-0.35% HSA buffer and resuspended to $2 \times 10^8$ cells/ml in the same buffer.

Platelet Aggregation Assay

The fixed activated platelets are incubated with a selected dose of the compound to be tested for platelet aggregation inhibition for one minute and aggregation initiated by addition of human fibrinogen to a final concentration of 250 µg/ml. A platelet aggregation profiler Model PAP-4 is used to record the platelet aggregation. The extent of inhibition of aggregation is expressed as the percentage of the rate of aggregation observed in the absence of inhibitor. $IC_{50}$, i.e., the amount of inhibitor required to reduce the aggregation rate by 50%, is then calculated for each compound (see, for example, Plow, E. F., et al., *Proc. Natl. Acad. Sci., USA* 82, 8057–8061 (1985)).

Fibrinogen-Binding Assay

Platelets are washed free of plasma constituents by the albumin density-gradient technique of Walsh, P. N., et al., *Br. J. Haematol.* 281–296 (1977), as modified by Trapani-Lombardo, V., et al., *J. Clin Invest.* 76, 1950–1958 (1985). In each experimental mixture platelets in modified Tyrode's buffer (Ruggeri, Z. M., et al., *J. Clin. Invest.* 72, 1–12 (1983)) are stimulated with human α-thrombin at 22°–25° C. for 10 minutes ($3.125 \times 10^{11}$ platelets per liter and thrombin at 0.1 NIH units/ml). Hirudin is then added at a 25-fold excess (unit/unit) for 5 minutes before addition of the $^{125}$I-labeled fibrinogen and the compound to be tested. After these additions, the final platelet count in the mixture is $1 \times 10^{11}$/liter. After incubation for an additional 30 minutes at 22°–25° C., bound and free ligand are separated by centrifuging 50 µl of the mixture through 300 µl of 20% sucrose at 12,000×g for 4 minutes. The platelet pellet is then separated from the rest of the mixture to determine platelet-bound radioactivity. Nonspecific binding is measured in mixtures containing an excess of unlabeled ligand. When binding curves are analyzed by Scatchard analysis, nonspecific binding is derived as a fitted parameter from the binding isotherm by means of a computerized program (Munson, P. J., *Methods Enzymol.* 92, 542–576 (1983)). To determine the concentration of each inhibitory compound necessary to inhibit 50% of fibrinogen binding to thrombin-stimulated platelets ($IC_{50}$), each compound is tested at 6 or more concentrations with $^{125}$I-labeled fibrinogen held at 0.176 µmol/liter (60 µg/ml). The $IC_{50}$ is derived by plotting residual fibrinogen binding against the logarithm of the sample compound's concentration.

Inhibition of ADP-Induced ex-vivo Platelet Aggregation

Experimental Protocol

Control blood samples are obtained 5–10 minutes prior to administration of the test compound in mongrel dogs weighing from 10 to 20 kg. The compound is administered intragasticly, via aqueous gavage, or orally, via gelatin capsule. Blood samples (5 ml) are then obtained at 30 minute intervals for 3 hours, and at 6, 12, and 24 hours after dosing. Each blood sample is obtained by venipuncture of the cephalic vein and is collected directly into a plastic syringe containing one part 3.8% trisodium citrate to nine parts blood.

Ex vivo canine platelet aggregation

The blood samples are centrifuged at 1000 rpm for 10 minutes to obtain platelet rich plasma (PRP). After removal of the PRP, the sample is centrifuged for an additional 10 minutes at 2000 rpm to obtain platelet poor plasma (PPP). Platelet count in the PRP is determined by using a Coulter Counter (Coulter Electronics, Hialeah, Fla.). If the concentration of platelets in the PRP is greater than 300,000 platelets/µl, then the PRP is diluted with PPP to adjust the platelet count to 300,000 platelets/µl. Aliquots of PRP (250 µl) are then placed in siliconized glass cuvettes (7.25×55 mm, Bio/Data Corp, Horsham, Pa.). Epinephrine (final concentration of 1 µM) is then added to the PRP, which is incubated for one minute at 37° C. A stimulator of platelet aggregation, ADP at a final concentration of 10 µM, is then added to the PRP. Platelet aggregation is monitored spectrophotometrically utilizing a light transmission aggregometer (Bio/Data Platelet Aggregation Profiler, Model PAP-4, Bio/Data Corp, Horsham, Pa.). For compound to be tested, the rate of change (slope) of light transmittance and the maximum light transmittance (maximum aggregation) is recorded in duplicate. Platelet aggregation data are reported as the percent decrease (mean±SEM) in slope or maximum aggregation as compared to data obtained from control PRP, which is prepared from blood samples obtained prior to administration of the test compound.

Compounds of the present invention exhibit marked activity in the foregoing tests and are considered useful in the prevention and treatment of thrombosis associated with certain disease states. Antithrombotic activity in the ex vivo canine platelet aggregation assay is predictive of such activity in humans (see, for example, Catalfamo, J. L., and Dodds, W. Jean, "Isolation of Platelets from Laboratory Animals", *Methods Enzymol.* 169, Part A, 27 (1989)). Results of testing of compounds of the present invention by the above methods are presented in the table below. Also presented in the table are comparative test results for 4-4 (piperidyl)butanoyl glycyl aspartyl tryptophan, i.e., the compound disclosed in European Patent Application Publication No. 0479,481.

| | | | | | | | | |
|---|---|---|---|---|---|---|---|---|
| 15 | 0.072 | 5 | 35 | 18 | | | | <20 |
| 14 | 0.019 | 5 | 100 | 100 | 100 | 100 | 95 | |
| 13 | | 5 | 100 | 100 | 25 | | | |
| 17 | 0.096 | | | | | | | |
| 18 | 0.104 | | | | | | | |
| 19 | 3.41 | | | | | | | |
| 20 | 1.37 | | | | | | | |
| 21 | 0.055 | | | | | | | |
| 22 | 0.09 | | | | | | | |
| 23 | 0.078 | | | | | | | |
| 24 | 0.129 | | | | | | | |
| 25 | 0.046 | | | | | | | |
| 26 | 0.029 | | | | | | | |
| 27 | 0.119 | | | | | | | |
| 28 | 0.048 | | | | | | | |
| 29 | 0.032 | | | | | | | |
| 30 | 0.07 | | | | | | | |
| 31 | 0.053 | | | | | | | |
| 32 | 0.052 | | | | | | | |
| 33 | 0.047 | | | | | | | |
| 34 | 0.074 | | | | | | | |
| (Compound of EPA '481) | 0.047 | 5 | 53 | <20 | | | | |

One skilled in the art will readily appreciate that the present invention is well adapted to carry out the objects and obtain the ends and advantages mentioned, as well as those inherent therein. The compounds, compositions, and methods described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

What is claimed is:

1. A compound of the formula

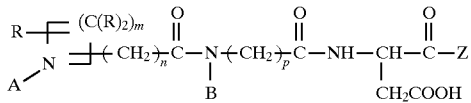

wherein:

A is -H, amidino, or substituted amidino;

B is alkyl, cycloalkyl, cycloalkylalkyl, alkylcycloalkyl, alkylcycloalkylalkyl, aryl, aralkyl, alkylaryl, or alkylaralkyl;

Z is 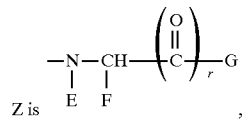

where

E is -H,

F is -H, alkyl, hydroxymethyl, 1-hydroxyethyl, mercaptomethyl, 2-methylthioethyl, carboxymethyl, 2-carboxyethyl, aminocarbonylmethyl, 2-aminocarbonylethyl, 4-aminobutyl, 3-aminopropyl, 3-guanidinopropyl, indol-3-ylmethyl, imidazol-3-ylmethyl, cycloalkyl, cycloalkylalkyl, cyclohexylcyclohexylmethyl, 1,2,3,4-tetrahydronaphth-5-ylmethyl, alkylcycloalkyl, alkylcycloalkylalkyl, aryl, substituted aryl, aralkyl, substituted aralkyl, heterocyclyl, substituted heterocyclyl, heterocyclylalkyl, substituted heterocyclylalkyl, wherein heterocyclyl is pyridyl, pyrimidyl or pyrrolidyl, or, F taken together with E and the nitrogen and carbon atoms through which E and F are linked, forms a 4-, 5-, 6-, or 7-membered azacycloalkane ring, wherein the azacycloalkane ring is optionally substituted with hydroxy, G is alkyl, cycloalkyl, cycloalkylalkyl, alkylcycloalkyl, alkylcycloalkylalkyl, aryl, substituted aryl, aralkyl, substituted aralkyl, heterocyclyl, substituted heterocyclyl, heterocyclylalkyl, substituted heterocyclylalkyl, wherein heterocyclyl is pyridyl, pyrimidyl or pyrrolidyl, $OR^1$, or $NR^1R^2$, where $R^1$ and $R^2$ are independently -H, alkyl, cycloalkyl, cycloalkylalkyl, alkylcycloalkyl, alkylcycloalkylalkyl, aryl, aralkyl, alkylaryl, or alkylaralkyl, r is 0 or 1;

R is H-, alkyl, aryl, or aralkyl;

m is 1 to 5;

n is 0 to 6; and p is 1 to 4;

or a pharmaceutically acceptable salt thereof.

2. A compound of claim 1 wherein

F is -H, alkyl, hydroxymethyl, 1-hydroxyethyl, mercaptomethyl, 2-methylthioethyl, carboxymethyl, 2-carboxyethyl, aminocarbonylmethyl, 2-aminocarbonylethyl, 4-aminobutyl, 3-aminopropyl, 3-guanidinopropyl, phenylmethyl, 4-hydroxyphenylmethyl, indol-3-ylmethyl, imidazol-3-ylmethyl, cycloalkyl, cycloalkylalkyl, cyclohexylcyclohexylmethyl, 1,2,3,4-tetrahydronaphth-5-ylmethyl, alklylcycloalkyl, alkylcycloalkylalkyl, aryl, substituted aryl, aralkyl, substitued aralkyl, heterocyclyl, substituted heterocyclyl, heterocyclylalkyl, substituted heterocyclylalkyl, wherein heterocyclyl is pyridyl, pyrimidyl or pyrrolidyl, or, F taken together with E and the nitrogen and carbon atoms through which E and F are linked, forms a 4-, 5-, 6-, or 7-membered azacycloalkane ring, wherein the azacycloalkane ring is optionally substituted with hydroxy, provided that when r is 1 and G is -$OR^1$, then F is other than -H, methyl, isopropyl, isobutyl, sec-butyl, hydroxymethyl, 1-hydroxyethyl, mercaptomethyl, 2-methylthioethyl, carboxymethyl, 2-carboxyethyl, aminocarbonylmethyl, 2-aminocarbonylethyl, 4-aminobutyl, 3-aminopropyl, 3-guanidinopropyl, phenylmethyl, 4-hydroxyphenylmethyl, indol-3-ylmethyl, or imidazol-3-ylmethyl, or the group

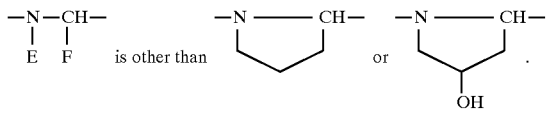

3. A compound of claim 2 wherein F is -H, alkyl, hydroxymethyl, 1-hydroxyethyl, mercaptomethyl, 2-methylthioethyl, carboxymethyl, 2-carboxyethyl, 4-aminobutyl, 3-guanidinopropyl, cycloalkyl, cycloalkylalkyl, alkylcycloalkyl, alkylcycloalkylalkyl, aryl, substituted aryl, aralkyl, substituted aralkyl, heterocyclyl, substituted heterocyclyl, heterocyclylalkyl, substituted heterocyclylalkyl, wherein heterocyclyl is pyridyl, pyrimidyl or pyrrolidyl, or, F taken together with E, and the nitrotgen and carbon atoms through which E and F are linked, forms a 4-, 5-, 6-, or 7-membered azacycloalkane ring, wherein the azacycloalkane ring is optionally substituted with hydroxy, provided that when r is 1 and G is -OR$^1$, then F is other than -H, methyl, isopropyl, isobutyl, sec-butyl, hydroxymethyl, 1-hydroxyethyl, mercaptomethyl, 2-methylthioethyl carboxymethyl, 2-carboxyethyl, 4-aminobutyl, 3-guanidinopropyl, phenylmethyl, 4-hydroxyphenylmethyl, or the group

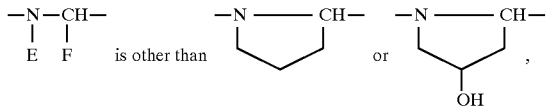

or a pharmaceutically acceptable salt thereof.

4. A compound of claim 3 wherein F is -H, alkyl, hydroxymethyl, 1-hydroxyethyl, mercaptomethyl, 2-methylthioethyl, carboxymethyl, 2-carboxyethyl, 4-aminobutyl, 3-guanidinopropyl, cycloalkyl, cycloalkylalkyl, alkylcycloalkyl, alkylcycloalkylalkyl, aryl, substituted aryl, aralkyl, substituted aralkyl, or, F taken together with E, and the nitrogen and carbon atoms through which E and F are linked, forms a 4-, 5-, 6-, or 7-membered azacycloalkane ring, wherein the azacycloalkane ring is optionally substituted with hydroxy, provided that when r is 1 and G is -OR$^1$, then F is other than -H, methyl, isopropyl, isobutyl, sec-butyl, hydroxymethyl, 1-hydroxyethyl, mercaptomethyl, 2-methylthioethyl, carboxymethyl, 2-carboxyethyl, 4-aminobutyl, 3-guanidinopropyl, phenylmethyl, 4-hydroxyphenylmethyl, or the group

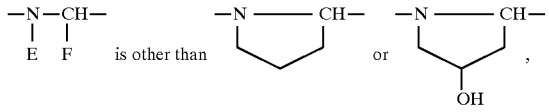

or a pharmaceutically acceptable salt thereof.

5. A compound of claim 4 wherein F is -H, alkyl, hydroxymethyl, 1-hydroxyethyl, mercaptomethyl, 2-methylthioethyl, carboxy methyl, 2-carboxyethyl, 4-aminobutyl, 3-guanidinopropyl, cycloalkyl, cycloalkylalkyyl, alkylcycloalkyl, alkylcycloalkylalkyl, or, F taken tog)ether with E, and the nitrogen and carbon atoms through which E and F are linked, forms a 4-, 5-, 6-, or 7-membered azacycloalkane ring, wherein the azacycloalkane ring, is optionally substituted with hydroxy, provided that when r is 1 and G is -OR$^1$, then F is other than -H, methyl, isopropyl, isobutyl, sec-butyl, hydroxymethyl, 1-hydroxyethyl, mercaptomethyl, 2-methylthioethyl, carboxymethyl, 2-carboxyethyl, 4-aminobutyl, 3-guanidinopropyl, or the group

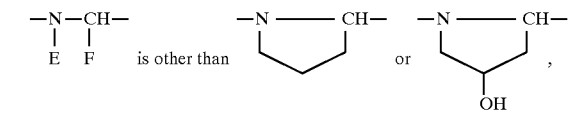

or a pharmaceutically acceptable salt thereof.

6. A compound of claim 5 wherein B is alkyl, cycloalkyl, cycloalkylalkyl, alkylcycloalkyl, or alkylcycloalkylalkyl.

7. A compound of claim 6 wherein R$^1$ and R$^2$ are independently -H, alkyl, cycloalkyl, cycloalkylalkyl, alkylcycloalkyl or alkylcycloalkylalkyl.

8. A pharmaceutical composition comprising an antithrombotic effective amount of a compound of claim 2 and a pharmaceutically acceptable carrier.

9. A compound of claim 1 of the formula

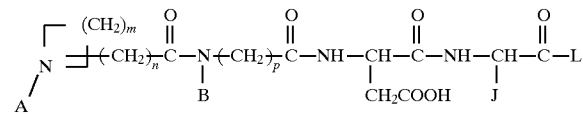

wherein:

A is -H or amidino,

B is alkyl, cycloalkyl, cycloalkylalkyl, alkylcycloalkyl, alkylcycloalkylalkyl, aryl, aralkyl, alkylaryl, alkylaralkyl, J is -H, alkyl, cycloalkyl, cycloalkylalkyl, alkylcycloalkyl, alkylcycloalkylalkyl, aryl, substituted aryl, aralkyl, substitued aralkyl, cyclohexylcyclohexylmethyl, or 1,2,3,4-tetrahydronaphth-5-ylmethyl, provided that when L is -OR$^1$, then J is other than -H, methyl, isopropyl, isobutyl, sec-butyl, phenylmethyl or 4-hydroxyphenylmethyl, L is OR$^1$, or NR$^1$R$^2$, where R$^1$ and R$^2$ are independently -H, alkyl, cycloalkyl, cycloalkylalkyl, alkylcycloalkyl, alkylcycloalkylalkyl, aryl, aralkyl, alkylaryl, or alkylaralkyl, m is 1 to 5, n is 2 to 6, and p is 1 or 2;

or a pharmaceutically acceptable salt thereof.

10. A compound of claim 9 wherein

A is -H,

B is alkyl, cycloalkyl, cycloalkylalkyl, alkylcycloalkyl, or alkylcycloalkylalkyl, J is -H, alkyl, cycloalkyl, cycloalkylalkyl, alkylcycloalkyl, alkylcycloalkylalkyl, or cyclohexylcyclohexylmethyl, provided that when L is -OR$^1$, then J is other than -H, methyl, isopropyl, isobutyl, sec-butyl, phenylmethiyl or 4-hydroxyplhenylmethyl, m is 3, and n is 3 or 4, or a pharmaceutically acceptable salt thereof.

11. A compound of claim 10 wherein

A is -H,

B is alkyl,

J is alkyl, cycloalkyl, or cycloalkylalkyl, or cyclohexylcyclohexylmethyl, provided that when L is -OR$^1$, then J is other than methyl, isopropyl, isobutyl, or sec-butyl, $R^1$ and $R^2$ are independently -H, alkyl, cycloalkyl, cycloalkylalkyl, alkylcycloalkyl, or alkylcycloalkylalkyl, m is 3, n is 3 or 4, and p is 1, or a pharmaceutically acceptable salt thereof.

12. A pharmaceutical composition comprising an antithrombotic effective amount of a compound of claim 9 and a pharmaceutically acceptable carrier.

13. A pharmaceutical composition comprising an antithrombotic effective amount of a compound of claim 1 and a pharmaceutically acceptable carrier.

14. A compound of claim 1 of the formula $$R \overset{(C(R)_2)_m}{\underset{A}{\diagdown}} N \text{---}(CH_2)_n\text{---}C(O)\text{---}N(B)\text{---}(CH_2)_p\text{---}C(O)\text{---}NH\text{---}CH(CH_2COOH)\text{---}C(O)\text{---}Z$$

wherein:

A is -H, amidino, or substituted amidino,

B is alkyl, cycloalkyl, cycloalkylalkyl, alkylcycloalkyl, alkylcycloalkylalkyl, aryl, aralkyl, alkylaryl, or alkylaralkyl;

Z is 
$$-N(E)\text{---}CH(F)\text{---}(C(O))_r\text{---}G,$$

where

E is -H,

F is -H, methyl, isopropyl, isobutyl, sec-butyl, hydroxymethyl, 1-hydroxyethyl, mercaptomethyl, 2-methylthioethyl, carboxymethyl, 2-carboxyethyl, aminocarbonylmethyl, 2-aminocarbonylethyl, 4-aminobutyl, 3-aminopropyl, 3-guanidinopropyl, phenylmethyl, 4-hydroxyphenylmethyl, indol-3-ylmethyl, imidazol-3-ylmethyl, or the group $$-N(E)\text{---}CH(F)\text{---} \quad \text{is} \quad -N\text{---}CH\text{---(ring)} \quad \text{or} \quad -N\text{---}CH\text{---(ring with OH)};$$

G is -OR$^1$ wherein R$^1$ is -H, alkyl, cycloalkyl, cycloalkylalkyl, alkylcycloalkyl, or alkylcycloalkylalkyl, r is 1;

R is -H, alkyl, aryl, or aralkyl;

m is 1 to 5;

n is 0 to 6; and p is 1 to 4;

or a pharmaceutically acceptable salt thereof.

15. A compound of claim 14 wherein F is -H, methyl, isopropyl, isobutyl, sec-butyl, hydroxymethyl, 1-hydroxyethyl, mercaptomethyl, 2-methylthioethyl, carboxymethyl, 2-carboxyethyl, 4-aminobutyl, 3-guanidinopropyl, or the group $$-N(E)\text{---}CH(F)\text{---} \quad \text{is} \quad -N\text{---}CH\text{---(ring)} \quad \text{or} \quad -N\text{---}CH\text{---(ring with OH)},$$

or a pharmaceutically acceptable salt thereof.

16. A compound of claim 15 wherein B is alkyl, cycloalkyl, cycloalkylalkyl, alkylcycloalkyl, or alkylcycloalkylalkyl.

17. A pharmaceutical composition comprising an antithrombotic effective amount of a compound of claim 14 and a pharmaceutically acceptable carrier.

18. A compound of claim 1 of the formula $$\underset{A}{\diagdown}N\text{---}\overset{(CH_2)_m}{\diagup}\text{---}(CH_2)_n\text{---}C(O)\text{---}N(B)\text{---}(CH_2)_p\text{---}C(O)\text{---}NH\text{---}CH(CH_2COOH)\text{---}C(O)\text{---}NH\text{---}CH(J)\text{---}C(O)\text{---}L$$

wherein:

A is -H or amidino:

B is alkyl, cycloalkyl, cycloalkylalkyl, alkylcycloalkyl, alkylcycloalkylalkyl, aryl, aralkyl, alkylaryl, or alkylaralkyl;

J is -H, methyl, isopropyl, isobutyl, sec-butyl;

L is -OR$^1$ wherein R$^1$ is -H, alkyl, cycloalkyl, cycloalkylalkyl, alkylcycloalkyl, or alkylcycloalkylalkyl, m is 1 to 5;

n is 2 to 6; and p is 1 or 2;

or a pharmaceutically acceptable salt thereof.

19. A compound of claim 18 wherein

A is -H;

B is alkyl, cycloalkyl, cycloalkylalkyl, alkylcycloalkyl, alkylcycloalkylalkyl;

m is 3; and n is 3 or 4;

or a pharmaceutically acceptable salt thereof.

20. A compound of claim 19 wherein

B is alkyl;

L is -OR$^1$ wherein R$^1$ is -H, alkyl, cycloalkyl, cycloalkylalkyl or alkylcycloalkylalkyl;

m is 3;

n is 3 or 4; and p is 1;

or a pharmaceutically acceptable salt thereof.

21. A pharmaceutical composition comprising an antithrombotic effective amount of a compound of claim 18 and a pharmaceutically acceptable carrier.

22. A compound which is

N-[N-[N-(4-(piperidin-4-yl)butanoyl)-N-ethylglycyl] aspartyl] valine,

N-[N-[N-(4-(piperidin-4-yl)butanoyl)-N-ethylglycyl] aspartyl]-D-valine,

N-[N-[N-(3-(piperidin-4-yl)propanoyl)-N-ethylglycyl] aspartyl] valine,

N-[N-[N-(5-(piperidin-4-yl)pentanoyl)-N-ethylglycyl] aspartyl] valine,

N-[N-[N-(4-(piperidin-4-yl)butanoyl)-N-ethylglycyl] aspartyl]-L-α-cyclohexyl glycine, N-[N-[N-(4-(piperidin-4-yl)butanoyl)-N-ethylglycyl] aspartyl]-β-cyclohexylalanine, N-[N-[N-(4-(piperidin-4-yl)butanoyl)-N-ethylglycyl] aspartyl] norleucine, N-[N-[N-(4-(piperidin-4-yl)butanoyl)-N-ethylglycyl] aspartyl]-L-α-(2,2-dimethyl)prop3-yl glycine, N-[N-[N-(4-(piperidin-4-yl)butanoyl)-N-ethylglycyl] aspartyl]-L-β-cis-decahydronaphth-2-ylalanine, N-[N-[N-(4-(piperidin-4-yl)butanoyl)-N-ethylglycyl] aspartyl]-α-aminocyclohexanecarboxylic acid, N-[N-[N-(4-(piperidin-4-yl)butanoyl)-N-ethylglycyl] aspartyl]-β-cyclohexyl-D-alaniine, N-[N-[N-(4-(piperidin-4-yl)butanoyl)-N-ethylglycyl] aspartyl]-β-decahydronaphth-1-ylalanine, N-[N-[N-(4-(piperidin-4-yl)butanoyl)-N-ethylglycyl] aspartyl]-β-cyclooctylalamine, N-[N-[N-(4-(piperidin-4-yl)butanoyl)-N-ethylglycyl] aspattyl]-β-adamant-1-ylalanine, N-[N-[N-(4-(piperidin-4-yl)butanoyl)-N-ethylglycyl] aspartyl]-β-(4-cyclohexyl)cyclohexylalanine, N-[N-[N-(4-(piperidin-4-yl)butanoyl)-N-ethylglycyl] aspartyl]-β-cycloheptylalanine, N-[N-[N-(4-(piperidin-4-yl)butanoyl)-N-ethylglycyl] aspartyl]-α-cyclohexylpropylglycine, N-[N-[N-(4-(piperidin-4-yl)butanoyl)-N-ethylglycyl] aspartyl]-β-cyclooctylmethylalanine, N-[N-[N-(4-(piperidin-4-yl)butanoyl)-N-ethylglycyl] aspartyl]-β-cyclopentylalanine N-[N-[N-(4-(piperidin-4-yl)butanoyl)-N-ethylglycyl] aspartyl]-L-β-decahydronaphth-1-yl alanine, N-[N-[N-(4-(piperidin-4-yl)butanoyl)-N-ethylglycyl] aspartyl]-L-α-(2-cyclohexylethyl)glycine, N-[N-[N-(4-(piperidin-4-yl)butanoyl)-N-ethylglycyl] aspartyl] phenylalanine, N-[N-[N-(4-(piperidin-4-yl)butanoyl)-N-ethylglycyl] aspartyl]-β-(1,2,3,4)-tetrahydronaphth-5-ylalanine, N-[N-[N-(4-(piperidin-4-yl)butanoyl)-N-ethylglycyl] aspartyl]-L-β-naphth-1-yl alanine, N-[N-[N-(4-(piperidin-4-yl)butanoyl)-N-ethylglycyl] aspartyl]-L-β-naphth-2-yl alanine, N-[N-[N-(4-(pipenidin-4-yl)butanoyl)-N-ethylglycyl] aspartyl]-L-β-cyclohexyl alanine amide, N-[N-[N-(4-(piperidin-4-yl)butanoyl)-N-ethylglycyl] aspartyl]-β-cyclooctylalanine amide, N-[N-[N-(4-(piperidin-4-yl)butanoyl)-N-ethylglycyl] aspartyl]-β-cyclohexylmethylalanine amide, N-[N-[N-(4-(piperidin-4-yl)butanoyl)-N-ethylglycyl] aspartyl]-β-cyclohexylalanine ethyl amiide, N-[N-[N-(4-(piperidin-4-yl)butanoyl)-N-ethylglycyl] aspartyl]-L-β-cyclohexyl alanine, ethyl ester, N-[N-[N-(4-(piperidin-4-yl)butanoyl)-N-ethylglycyl] aspartyl]-β-cyclohexylmethylalanine ethyl ester, 3-Adamant-1-ylpropyl-N-[N-(4-(piperidin-4-yl) butanoyl)-N-ethylglycyl]aspartate, 2-cyclohexyl-N-[N-[N-(4-(piperidin-4-yl)butanoyl)-N-ethylglycyl]aspartyl]-ethylamine, or N-[N-[N-(4-(piperidin-4-yl)butanoyl)-N-ethylglycyl] aspartyl]-α-cyclohexylmethylethanolamine, or a pharmaceutically acceptable salt thereof.

23. A pharmaceutical composition comprising an antithrombotic effective amount of a compound of claim 22 and a phanmaceutically acceptable carrier.

24. A method for the prevention or treatment of thrombosis in a mammal in need of such therapy comprising the administration of a therapeutically effective amount of a compound of claim 22.

25. A method for the prevention or treatment of thrombosis in a mammal in need of such therapy comprising the administration of a therapeutically effective amount of the composition of claim 23.

26. A method for the prevention or treatment of thrombosis in a mammal in need of such therapy comprising the administration of a therapeutically effective amount of a compound of claim 2.

27. A method for the prevention or treatment of thrombosis in a mammal in need of such therapy comprising the administration of a therapeutically effective amount of the composition of claim 8.

28. A method for the treatment of thrombosis in a mammal in need of such therapy comprising the administration of a therapeutically effective amount of a compound of claim 9.

29. A method for the prevention or treatment of thrombosis in a mammal in need of such therapy comprising the administration of a therapeutically effective amount of the composition of claim 14.

30. A method for the prevention or treatment of thrombosis in a mammal in need of such therapy comprising the administration of a therapeutically effective amount of the composition of claim 13.

31. A method for the treatment of thrombosis in a mammal in need of such therapy comprising the administration of a therapeutically effective amount of a compound of claim 1.

32. A method for the prevention or treatment of thrombosis in a mammal in need of such therapy comprising the administration of a therapeutically effective amount of a compound of claim 14.

33. A method for the prevention or treatment of thrombosis in a mammal in need of such therapy comprising the administration of a therapeutically effective amount of the composition of claim 17.

34. A method for the prevention or treatment of thrombosis in a mammal in need of such therapy comprising the administration of a therapeutically effective amount of a compound of claim 18.

35. A method for the prevention or treatment of thrombosis in a mammal in need of such therapy comprising the administration of a therapeutically effective amount of the composition of claim 21.

* * * * *